US011864780B2

(12) United States Patent
McGuckin, Jr. et al.

(10) Patent No.: US 11,864,780 B2
(45) Date of Patent: Jan. 9, 2024

(54) ATHERECTOMY DEVICE

(71) Applicant: Rex Medical, L.P., Conshohocken, PA (US)

(72) Inventors: James F. McGuckin, Jr., Radnor, PA (US); John D. Leedle, Chicago, IL (US); Colin Valentis, Lansdale, PA (US); Jenna Rose Israel, Philadelphia, PA (US); Aaron Larry Snyder, West Chester, PA (US)

(73) Assignee: REX MEDICAL, L.P., Conshohocken, PA (US)

( * ) Notice: Subject to any disclaimer, the term of this patent is extended or adjusted under 35 U.S.C. 154(b) by 198 days.

(21) Appl. No.: 17/326,478

(22) Filed: May 21, 2021

(65) Prior Publication Data
US 2021/0290258 A1  Sep. 23, 2021

Related U.S. Application Data

(63) Continuation of application No. 16/355,806, filed on Mar. 17, 2019, now Pat. No. 11,020,134, which is a
(Continued)

(51) Int. Cl.
*A61B 17/22* (2006.01)
*A61B 17/3207* (2006.01)
*A61B 17/00* (2006.01)

(52) U.S. Cl.
CPC ........ *A61B 17/22* (2013.01); *A61B 17/00234* (2013.01); *A61B 17/3207* (2013.01);
(Continued)

(58) Field of Classification Search
CPC .............. A61B 17/22; A61B 17/00234; A61B 17/320758; A61B 17/3207;
(Continued)

(56) References Cited

U.S. PATENT DOCUMENTS

| 4,445,509 A | 5/1984 | Auth |
| 4,883,458 A | 11/1989 | Shiber |

(Continued)

FOREIGN PATENT DOCUMENTS

| CN | 102670283 | 9/2012 |
| EP | 2 913 012 | 9/2015 |

(Continued)

OTHER PUBLICATIONS

The Extended European Search Report Application No. 15155876.4 dated Jul. 6, 2015.
(Continued)

*Primary Examiner* — Julian W Woo
(74) *Attorney, Agent, or Firm* — Neil D. Gershon

(57) ABSTRACT

An atherectomy device for removing deposits such as plaque from an interior of a vessel including an outer member, an inner member and a rotatable shaft positioned for rotational movement within the inner member. The outer and inner members are fixed axially. A rotatable tip is mounted to the distal region of the rotatable shaft for rotation about its longitudinal axis upon rotation of the shaft to remove deposits from the vessel.

18 Claims, 25 Drawing Sheets

Related U.S. Application Data continuation of application No. 15/442,584, filed on Feb. 24, 2017, now Pat. No. 10,307,175.

(60) Provisional application No. 62/313,712, filed on Mar. 26, 2016.

(52) U.S. Cl.
CPC ............ *A61B 17/320758* (2013.01); *A61B 2017/00292* (2013.01); *A61B 2017/00685* (2013.01); *A61B 2017/22001* (2013.01); *A61B 2017/22079* (2013.01); *A61B 2217/005* (2013.01); *A61B 2217/007* (2013.01)

(58) Field of Classification Search
CPC ........... A61B 2017/22001; A61B 2017/00292; A61B 2017/22079; A61B 2217/007; A61B 2217/005

See application file for complete search history.

(56) References Cited

U.S. PATENT DOCUMENTS

| | | | |
|---|---|---|---|
| 4,957,482 A | 9/1990 | Shiber | |
| 4,979,939 A | 12/1990 | Shiber | |
| 4,990,134 A | 2/1991 | Auth | |
| 5,019,089 A | 5/1991 | Farr | |
| 5,047,040 A | 9/1991 | Simpson | |
| 5,114,399 A | 5/1992 | Kovalcheck | |
| 5,217,474 A | 6/1993 | Zacca et al. | |
| 5,273,526 A | 12/1993 | Dance | |
| 5,287,858 A | 2/1994 | Hammerslag | |
| 5,306,244 A | 4/1994 | Shiber | |
| 5,308,354 A | 5/1994 | Zacca | |
| 5,312,427 A | 5/1994 | Shturman | |
| 5,314,438 A | 5/1994 | Shturman | |
| 5,356,418 A | 10/1994 | Shturman | |
| 5,490,859 A | 2/1996 | Mische | |
| 5,584,843 A | 12/1996 | Wulfman | |
| 5,632,755 A | 5/1997 | Nordgren et al. | |
| 5,653,696 A | 8/1997 | Shiber | |
| 5,667,490 A | 9/1997 | Keith | |
| 5,681,336 A | 10/1997 | Clement et al. | |
| 5,728,129 A | 3/1998 | Summers | |
| 5,779,721 A | 7/1998 | Nash | |
| 5,794,626 A | 8/1998 | Kieturakis | |
| 5,873,882 A | 2/1999 | Straub et al. | |
| 5,876,414 A | 3/1999 | Straub | |
| 5,879,361 A | 3/1999 | Nash | |
| 5,938,670 A | 8/1999 | Keith et al. | |
| 5,938,672 A | 8/1999 | Nash | |
| 5,951,581 A | 9/1999 | Saadat | |
| 5,976,165 A | 11/1999 | Ball et al. | |
| 6,001,112 A | 12/1999 | Taylor | |
| 6,015,420 A | 1/2000 | Wulfman et al. | |
| 6,146,395 A | 1/2000 | Kanz et al. | |
| 6,066,152 A | 5/2000 | Strauss et al. | |
| 6,077,282 A | 6/2000 | Shturman et al. | |
| 6,080,170 A | 6/2000 | Nash et al. | |
| 6,090,118 A | 7/2000 | McGuckin, Jr. | |
| 6,113,615 A | 9/2000 | Wulfman | |
| 6,132,444 A | 10/2000 | Shturman | |
| 6,156,046 A | 12/2000 | Passafaro et al. | |
| 6,156,048 A | 12/2000 | Wulfman et al. | |
| 6,183,487 B1 | 2/2001 | Barry et al. | |
| 6,206,898 B1 | 3/2001 | Honeycutt et al. | |
| 6,270,509 B1 | 8/2001 | Barry et al. | |
| 6,299,623 B1 | 10/2001 | Wulfman | |
| 6,443,967 B1 | 9/2002 | Kadavy et al. | |
| 6,454,779 B1 | 9/2002 | Taylor | |
| 6,482,216 B1 | 11/2002 | Hiblar et al. | |
| 6,491,660 B2 | 12/2002 | Guo et al. | |
| 6,494,890 B1 | 12/2002 | Shturman et al. | |
| 6,497,711 B1 | 12/2002 | Plaia et al. | |
| 6,565,588 B1 | 5/2003 | Clement | |
| 6,569,147 B1 | 5/2003 | Evans et al. | |
| 6,569,177 B1 | 5/2003 | Dillard et al. | |
| 6,572,630 B1 | 6/2003 | McGuckin, Jr. et al. | |
| 6,579,298 B1 | 6/2003 | Bruneau et al. | |
| 6,579,299 B2 | 6/2003 | McGuckin, Jr. et al. | |
| 6,596,005 B1 | 7/2003 | Kanz et al. | |
| 6,602,264 B1 | 8/2003 | McGuckin, Jr. | |
| 6,626,890 B2 | 9/2003 | Nguyen et al. | |
| 6,632,230 B2 | 10/2003 | Barry | |
| 6,652,546 B1 | 11/2003 | Nash et al. | |
| 6,702,830 B1 | 3/2004 | Demarais et al. | |
| 6,752,630 B2 | 6/2004 | Roetzer | |
| 6,808,531 B2 | 10/2004 | Lafontaine et al. | |
| 6,824,550 B1 | 11/2004 | Noriega et al. | |
| 6,830,577 B2 | 12/2004 | Nash et al. | |
| 6,843,797 B2 | 1/2005 | Nash et al. | |
| 6,905,505 B2 | 6/2005 | Nash et al. | |
| 6,926,725 B2 | 8/2005 | Cooke et al. | |
| 6,936,056 B2 | 8/2005 | Nash et al. | |
| 7,037,316 B2 | 5/2006 | McGuckin, Jr. et al. | |
| 7,172,610 B2 | 2/2007 | Heitzmann et al. | |
| 7,479,147 B2 | 1/2009 | Honeycutt et al. | |
| 7,534,249 B2 | 5/2009 | Nash et al. | |
| 7,645,261 B2 | 1/2010 | Hinchliffe | |
| 7,655,016 B2 | 2/2010 | Demarais | |
| 7,666,161 B2 | 2/2010 | Nash et al. | |
| 7,713,231 B2 | 5/2010 | Wulfman et al. | |
| 7,771,445 B2 | 8/2010 | Heitzmann et al. | |
| 7,833,239 B2 | 11/2010 | Nash | |
| 8,062,317 B2 | 1/2011 | McGuckin, Jr. et al. | |
| 7,905,896 B2 | 3/2011 | Straub | |
| 7,959,608 B2 | 6/2011 | Nash et al. | |
| 7,976,528 B2 | 7/2011 | Nash et al. | |
| 7,981,128 B2 | 7/2011 | To et al. | |
| 7,981,129 B2 | 7/2011 | Nash et al. | |
| 8,007,506 B2 | 8/2011 | To et al. | |
| 8,109,954 B2 | 2/2012 | Shturman | |
| 8,142,458 B2 | 3/2012 | Shturman | |
| 8,226,673 B2 | 7/2012 | Nash et al. | |
| 8,236,016 B2 | 8/2012 | To et al. | |
| 8,323,240 B2 | 12/2012 | Wulfman et al. | |
| 8,348,965 B2 | 1/2013 | Prudnikov et al. | |
| 8,353,922 B2 | 1/2013 | Noriega | |
| 8,353,923 B2 | 1/2013 | Shturman | |
| 8,361,094 B2 | 1/2013 | To et al. | |
| 8,361,097 B2 | 1/2013 | Patel et al. | |
| 8,388,582 B2 | 3/2013 | Eubanks et al. | |
| 8,414,543 B2 | 4/2013 | McGuckin, Jr. et al. | |
| 8,439,937 B2 | 5/2013 | Montague et al. | |
| 8,465,511 B2 | 6/2013 | McGuckin, Jr. et al. | |
| 8,475,484 B2 | 7/2013 | Wulfman et al. | |
| 8,551,128 B2 | 10/2013 | Hanson et al. | |
| 8,568,432 B2 | 10/2013 | Straub | |
| 8,574,249 B2 | 11/2013 | Moberg | |
| 8,579,851 B2 | 11/2013 | Cull | |
| 8,597,313 B2 | 12/2013 | Thatcher et al. | |
| 8,628,549 B2 | 1/2014 | To et al. | |
| 8,628,550 B2 | 1/2014 | Narveson et al. | |
| 8,628,551 B2 | 1/2014 | Hanson et al. | |
| 8,632,557 B2 | 1/2014 | Thatcher et al. | |
| 8,663,259 B2 | 3/2014 | Levine et al. | |
| 8,663,261 B2 | 3/2014 | Shturman | |
| 8,702,735 B2 | 4/2014 | Rivers | |
| 8,758,377 B2 | 6/2014 | Rivers et al. | |
| 8,764,779 B2 | 7/2014 | Levine et al. | |
| 8,795,303 B2 | 8/2014 | McBroom et al. | |
| 8,795,304 B2 | 8/2014 | Svendsen et al. | |
| 8,795,306 B2 | 8/2014 | Smith et al. | |
| 8,882,680 B2 | 11/2014 | Furlong et al. | |
| 8,888,801 B2 | 11/2014 | To et al. | |
| 8,920,402 B2 | 12/2014 | Nash et al. | |
| 9,023,070 B2 | 5/2015 | Levine et al. | |
| 9,028,424 B2 | 5/2015 | Furlong et al. | |
| 9,033,864 B2 | 5/2015 | Furlong et al. | |
| 9,033,895 B2 | 5/2015 | Furlong et al. | |
| 9,050,126 B2 | 6/2015 | Rivers et al. | |
| 9,055,966 B2 | 6/2015 | Cambronne et al. | |
| 9,072,505 B2 | 7/2015 | Furlong et al. | |
| 9,113,945 B2 | 8/2015 | Malla et al. | |

(56) References Cited

U.S. PATENT DOCUMENTS

| | | | |
|---|---|---|---|
| 9,119,660 B2 | 9/2015 | Rivers et al. | |
| 9,119,661 B2 | 9/2015 | Rivers et al. | |
| 9,211,138 B2 | 12/2015 | Shturman | |
| 9,320,535 B2 | 4/2016 | Zaretzka | |
| 9,675,376 B2 | 6/2017 | To | |
| 11,020,134 B2 * | 6/2021 | McGuckin, Jr. | ............................ A61B 17/320758 |
| 2001/0037121 A1 | 11/2001 | McGuckin, Jr. et al. | |
| 2002/0007190 A1 | 1/2002 | Wulfman et al. | |
| 2002/0099367 A1 | 7/2002 | Guo et al. | |
| 2002/0138088 A1 | 9/2002 | Nash | |
| 2003/0125757 A1 | 7/2003 | Patel | |
| 2003/0199889 A1 | 10/2003 | Kanz et al. | |
| 2004/0219028 A1 | 11/2004 | Demarais et al. | |
| 2004/0243162 A1 | 12/2004 | Wulfman et al. | |
| 2005/0080478 A1 | 4/2005 | Barongan | |
| 2005/0119678 A1 | 6/2005 | O'Brien | |
| 2005/0149084 A1 | 7/2005 | Kanz et al. | |
| 2007/0162062 A1 | 7/2007 | Norton | |
| 2008/0004643 A1 | 1/2008 | To et al. | |
| 2009/0018565 A1 | 1/2009 | To et al. | |
| 2009/0024085 A1 | 1/2009 | To et al. | |
| 2011/0040315 A1 | 2/2011 | To et al. | |
| 2011/0106051 A1 | 5/2011 | Saab | |
| 2011/0270289 A1 | 11/2011 | To et al. | |
| 2012/0071907 A1 | 3/2012 | Pintor et al. | |
| 2012/0130410 A1 | 5/2012 | Tal et al. | |
| 2012/0211542 A1 | 8/2012 | Racenet | |
| 2013/0018398 A1 | 1/2013 | Rivers et al. | |
| 2013/0018399 A1 | 1/2013 | Rivers et al. | |
| 2013/0023913 A1 | 1/2013 | Rivers et al. | |
| 2013/0103046 A1 | 4/2013 | Shiber | |
| 2013/0178868 A1 | 7/2013 | Roh | |
| 2013/0245704 A1 | 9/2013 | Koltz et al. | |
| 2013/0253552 A1 | 9/2013 | Schoenle et al. | |
| 2014/0148830 A1 | 5/2014 | Bowman | |
| 2014/0200599 A1 | 7/2014 | Shiber | |
| 2014/0316451 A1 | 10/2014 | Higgins et al. | |
| 2014/0330286 A1 | 11/2014 | Wallace | |
| 2015/0051626 A1 | 2/2015 | Rivers et al. | |
| 2015/0094748 A1 | 4/2015 | Nash et al. | |
| 2015/0164542 A1 | 6/2015 | Wulfman et al. | |
| 2015/0245851 A1 | 9/2015 | McGuckin, Jr. | |
| 2015/0342682 A1 | 12/2015 | Bowe | |

FOREIGN PATENT DOCUMENTS

| | | |
|---|---|---|
| NL | 1034242 | 8/2008 |
| WO | WO 1994/10919 | 5/1994 |
| WO | WO 1998/004199 | 2/1998 |
| WO | WO 2001/019444 | 3/2001 |
| WO | WO 2001/076680 | 10/2001 |
| WO | WO 2002/026289 | 4/2002 |
| WO | WO 2008/097993 | 8/2008 |
| WO | WO 2008/155759 | 12/2008 |
| WO | WO 2012/088167 | 6/2012 |
| WO | WO 2014/91881 | 6/2014 |
| WO | WO 2014/163942 | 10/2014 |

OTHER PUBLICATIONS

The Extended European Search Report Application No. 15200337.2 dated Apr. 28, 2016.
The Extended European Search Report Application No. 15200337.2 dated Nov. 18, 2020.
The Extended European Search Report Application No. 16187574.5 dated Jan. 30, 2017.
The Extended European Search Report Application No. 17161776.4-1659 dated Jul. 2017.

* cited by examiner

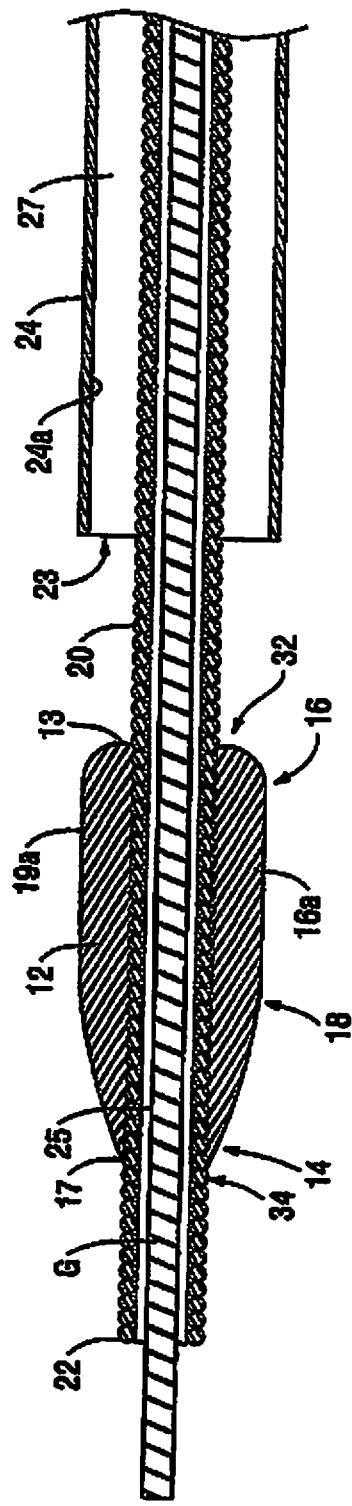
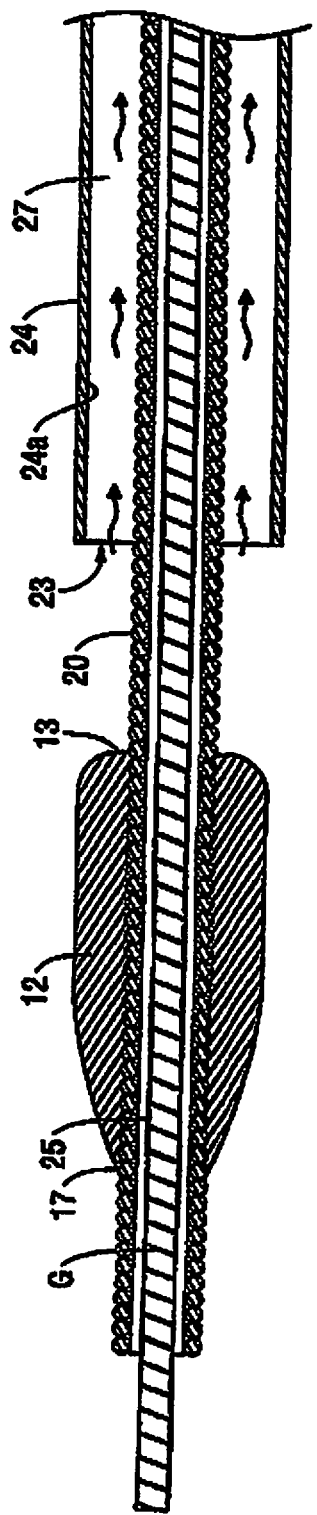

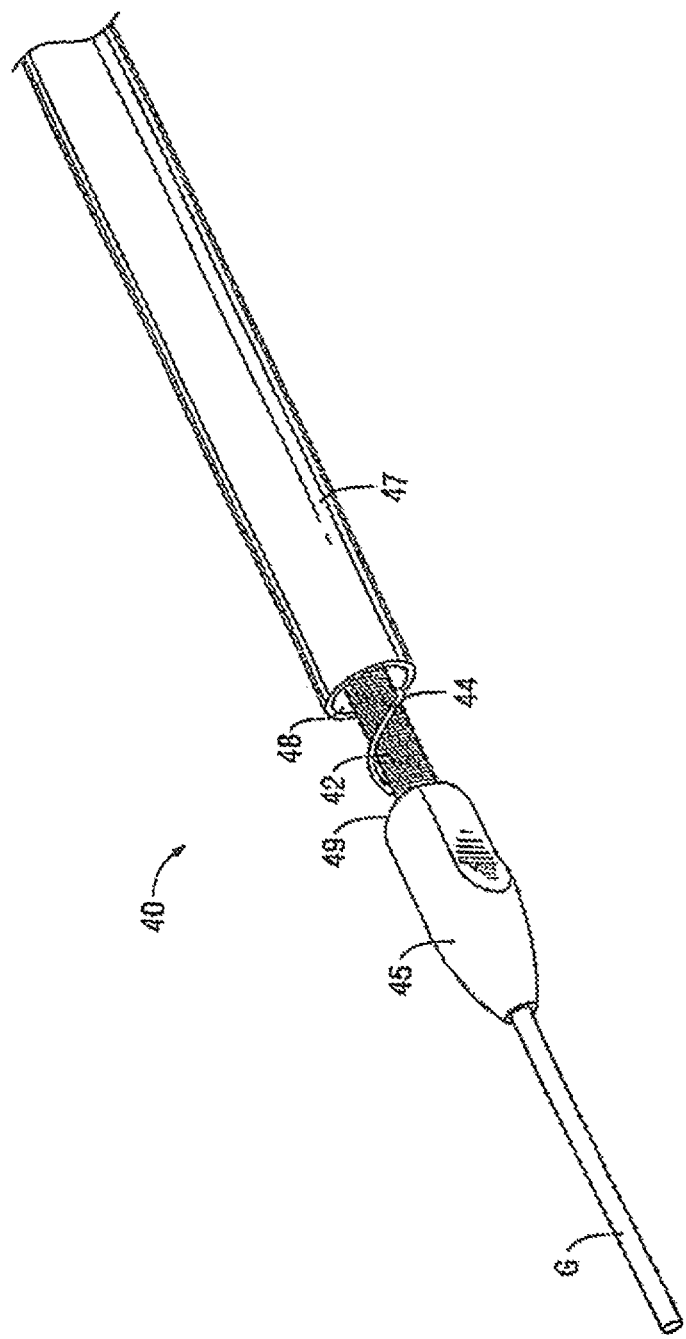

ATHERECTOMY DEVICE

This application is a continuation of application Ser. No. 16/355,806, filed Mar. 17, 2019, now U.S. Pat. No. 11,020,134, which is a continuation of application Ser. No. 15/442,584, filed Feb. 24, 2017, now U.S. Pat. No. 10,307,175, which claims priority from provisional application 62/313,712, filed Mar. 26, 2016. The entire contents of each of these applications are incorporated herein by reference.

BACKGROUND

Technical Field

This application relates to a vascular surgical apparatus, and more particularly to a minimally invasive device for removing plaque or other deposits from the interior of a vessel.

Background of Related Art

The vascular disease of atherosclerosis is the buildup of plaque or substances inside the vessel wall which reduces the size of the passageway through the vessel, thereby restricting blood flow. Such constriction or narrowing of the passage in the vessel is referred to as stenosis. In the case of peripheral vascular disease, which is atherosclerosis of the vascular extremities, if the vessel constriction is left untreated, the resulting insufficient blood flow can cause claudication and possibly require amputation of the patient's limb. In the case of coronary artery disease, if left untreated, the blood flow through the coronary artery to the myocardium will become inadequate causing myocardial infarction and possibly leading to stroke and even death.

There are currently several different treatments for treating arterial disease. The most invasive treatment is major surgery. With peripheral vascular diseases, such as occlusion of the tibial artery, major surgery involves implantation and attachment of a bypass graft to the artery so the blood flow will bypass the occlusion. The surgery involves a large incision, e.g., a 10 inch incision in the leg, is expensive and time consuming for the surgeon, increases patient pain and discomfort, results in a long patient recovery time, and has the increased risk of infection with the synthetic graft.

Major surgery for treating coronary artery disease is even more complex. In this surgery, commonly referred to as open heart surgery, a bypass graft connects the heart to the vessel downstream of the occlusion, thereby bypassing the blockage. Bypass surgery requires opening the patient's chest, is complex, has inherent risks to the patient, is expensive and requires lengthy patient recovery time. Bypass surgery also requires use of a heart lung machine to pump the blood as the heart is stopped, which has its own risks and disadvantages. Oftentimes, the saphenous vein in the patient's leg must be utilized as a bypass graft, requiring the additional invasive leg incision which further complicates the procedure, increases surgery time, lengthens the patient's recovery time, can be painful to the patient, and increases the risk of infection.

Attempts to minimize the invasiveness of coronary bypass surgery are currently being utilized in certain instances. These typically include creating a "window approach" to the heart. Although the window approach may reduce patient trauma and recovery time relative to open heart surgery, it still requires major surgery, and is a complicated and difficult surgery to perform due to limited access and limited instrumentation for successfully performing the operation. Attempts to avoid the use of a heart lung machine by using heart stabilization methods has become more accepted, but again, this does not avoid major surgery.

Due to the invasiveness and potential for complications with major peripheral or coronary vascular surgery, minimally invasive procedures have been developed. Balloon angioplasty is one of the minimally invasive methods for treating vessel occlusion and obstructions. A catheter having a balloon is inserted through the access artery, e.g., the femoral artery in the patient's leg or the radial artery in the arm, and advanced through the vascular system to the occluded site over a guidewire. The deflated balloon is placed at the occlusion and inflated to crack and stretch the plaque and other deposits to expand the opening in the vessel. Balloon angioplasty, especially in coronary surgery, is frequently immediately followed by insertion of a stent, a small metallic expandable device which is placed inside the vessel wall to retain the opening which was created by the balloon. Balloon angioplasty has several drawbacks including difficulty in forcing the balloon through the partially occluded passageway if there is hard occlusion, the risk involved in cutting off blood flow when the balloon is fully inflated, the frequency of restenosis after a short period of time since the plaque is essentially stretched or cracked and not removed from the vessel wall or because of the development of intimal hyperplasia and the possibility of balloon rupture when used in calcified lesions.

Another minimally invasive technique used to treat arteriosclerosis is referred to as atherectomy and involves removal of the plaque by a cutting or abrading instrument. This technique provides a minimally invasive alternative to the bypass surgery techniques described above and can provide an advantage over balloon angioplasty methods in certain instances. Atherectomy procedures typically involve inserting a cutting or ablating device through the access artery, e.g., the femoral artery or the radial artery, and advancing it over a guidewire through the vascular system to the occluded region, and rotating the device at high speed to cut through or ablate the plaque. The removed plaque or material can then be suctioned out of the vessel or be of such fine diameter that it is cleared by the reticuloendothelial system. Removal of the plaque in an atherectomy procedure has an advantage over balloon angioplasty plaque displacement since it debulks the material.

Examples of atherectomy devices in the prior art include U.S. Pat. Nos. 4,990,134, 5,681,336, 5,938,670, and 6,015,420. These devices have elliptical shaped tips which are rotated at high speeds to cut away the plaque and other deposits on the interior vessel wall. A well-known device is marketed by Boston Scientific Corp. and referred to as the Rotablator. As can be appreciated, in these devices, the region of plaque removal is dictated by the outer diameter of the cutting tip (burr) since only portions of the plaque contacted by the rotating tip are removed. The greater the area of plaque removed, the larger the passageway created through the vessel and the better the resulting blood flow.

U.S. Pat. Nos. 5,217,474 and 6,096,054 disclose expandable cutting tips. These tips however are quite complex and require additional expansion and contraction steps by the surgeon.

U.S. Pat. No. 6,676,698 discloses an atherectomy device designed to obtain an optimal balance between the competing objectives of the smallest introducer sheath size to facilitate insertion and reduce trauma to the vessel and the largest atherectomy tip size to remove a larger region of plaque or other deposits from the vessel wall.

However, it would be advantageous to enhance the breaking up and removal of the small particles in atherectomy procedures.

SUMMARY

The present invention provides in one aspect an atherectomy device for removing deposits such as plaque from an interior of a vessel comprising a housing, an outer member extending from the housing and having a distal end and a rotatable shaft positioned for rotational movement within the outer member, the shaft having a longitudinal axis, a distal region and a distalmost edge. The outer member is fixed axially with respect to the housing. A rotatable tip has a proximal end and a distal end. The proximal end of the rotatable tip is positioned distally of the distal end of the outer member to create a gap between the proximal end of the rotatable tip and the distalmost edge of the outer member. The rotatable tip is mounted to the distal region of the rotatable shaft. The rotatable tip has a longitudinal axis and is mounted to the rotatable shaft for rotation about its longitudinal axis upon rotation of the shaft. The shaft includes a guidewire lumen for receiving a guidewire to enable over the wire insertion of the device.

In some embodiments, the device includes an auger positioned on the rotatable shaft, the auger positioned proximally of the rotatable tip and extending along the outer shaft, wherein rotation of the shaft rotates the auger to move particles abraded by the tip proximally into the outer member.

In some embodiments, a portion of the auger is exposed between the proximal end of the rotatable tip and the distalmost edge of the outer member; in other embodiments, the auger is positioned within the outer member such that it is not exposed between the proximal end of the rotatable tip and the distalmost edge of the outer member.

A coating can be provided over at least a portion of the rotatable shaft and/or auger.

A motor for rotating the rotatable shaft can be provided positioned within the housing.

In some embodiments, particles are aspirated through the outer member in the space between the rotatable shaft and an inner wall of the outer member.

In some embodiments, the rotatable tip can be mounted proximal of the distalmost end of the rotatable shaft.

The tip can have a lumen extending therethrough dimensioned to receive the rotatable shaft.

In some embodiments, the rotatable tip is composed of first and second components, e.g., halves, the components radially spaced from each other. In some embodiments, the first component is composed of a material having a density greater than the second component. In some embodiments, the first component has a portion removed so it is composed of less material than the second component.

In accordance with another aspect of the present disclosure a method for removing deposits such as plaque from an interior of a vessel is provided. The method comprises the steps of:

providing an introducer sheath having an internal diameter;

providing a deposit removal device including an outer member, a rotatable shaft and a rotatable tip at a distal portion of the rotatable shaft, the outer member axially fixed (or substantially axially fixed) to maintain a fixed (or substantially fixed) spacing between the distal end of the outer member and proximal end of the rotatable tip;

inserting the introducer sheath through a skin incision and into a vessel;

advancing the rotatable tip adjacent the deposits to be removed; and actuating a motor to rotate the rotatable tip at high speed by rotation of the rotatable shaft to contact and remove the deposits, the rotatable tip rotating to remove deposits; and aspirating deposits through a space in the outer member between the shaft and an inner wall of the outer member during rotation of the rotatable shaft.

In some embodiments, the rotatable shaft can have an auger thereon so the step of rotating the rotatable shaft causes the auger to direct particles proximally within the outer member.

The method in some embodiments further includes the step of applying a vacuum to aspirate proximally deposits removed by rotational movement of the tip. The method can further include the step of inserting the tip over a guidewire.

In accordance with another aspect of the present disclosure, an atherectomy device for removing deposits such as plaque from an interior of a vessel is provided comprising:

a housing;

an outer member extending from the housing and having a distal end and a first lumen terminating proximal of the distal end of the outer member and a side opening communicating with the first lumen for fluid infusion;

an inner member having a distal end and positioned within the first lumen of the outer member, the inner member having a second lumen terminating at the distal end of the inner member and having an opening for aspiration of particles proximally within the second lumen, the side opening in the outer member communicating with the second lumen for fluid infusion from the first lumen into the second lumen;

a rotatable shaft positioned for rotational movement within the second lumen of the inner member; and a rotatable tip positioned at the distal region of the rotatable shaft and spaced distally from the distal end of the inner member, the rotatable tip rotatable by a motor to remove the deposits from the vessel for aspiration through the second lumen of the inner member.

In preferred embodiments, the outer member is axially fixed (or substantially axially fixed) with respect to the housing and the inner member is axially fixed (or substantially axially fixed) with respect to the outer member.

In some embodiments, the rotatable tip has a lumen to receive the rotatable shaft, the lumen having a first region having a first internal diameter and a second region having a second internal diameter greater than the first internal diameter, the second region being proximal of the first region. In some embodiments, the rotatable shaft includes a guidewire lumen for receiving a guidewire to enable over the wire insertion of the device, the guidewire lumen axially aligned with the lumen in the rotatable tip.

The atherectomy device can in some embodiments include an auger positioned on the rotatable shaft, the auger positioned proximally of the rotatable tip and extending along the rotatable shaft, wherein rotation of the rotatable shaft rotates the auger to move deposits macerated by the rotatable tip proximally into the outer member. The augur can aspirate the fluid received from the first lumen through the second lumen of the inner member. In some embodiments, a portion of the auger is exposed between a proximalmost edge of the rotatable tip and a distalmost edge of the inner member; in other embodiments the auger is not exposed between the proximalmost end of the rotatable tip and a distalmost edge of the outer member.

The device can include a coating over at least a portion of the rotatable shaft and auger.

In some embodiments, the inner member comprises a first inner member and a second inner member positioned distal of the first inner member, and a proximal end of the second inner member is spaced from a distal end of the first inner member to provide a gap for entry of fluid from the first lumen into the second lumen of the first inner member. In some embodiments, the outer member has an end wall to terminate the first lumen proximal of the distal end of the outer member to terminate distal flow of fluid for redirection through the side opening and the second lumen of the inner lumen. In some embodiments, the outer member is formed by a first and second tube.

In some embodiments, infusion of fluid from the first lumen is prevented from entering the vessel when aspiration is on to provide a closed system.

In some embodiments, the rotatable tip is maintained at a fixed distance from the inner member during insertion and during use of the atherectomy device.

In some embodiments, the atherectomy device includes a first hub and a second hub connected to the first hub, the first hub in fluid communication with the first lumen of the outer member for fluid infusion into the first lumen and the second hub in fluid communication with the second lumen of the inner member for aspiration of particles proximally though the second lumen. In some embodiments, the first and second hubs are coaxial with the outer member and inner member.

In accordance with another aspect of the present invention, an atherectomy device for removing deposits such as plaque from an interior of a vessel is provided comprising:
  a housing;
  an outer member extending from the housing and having a distal end, the outer member having a first lumen and a side opening, the first lumen terminating proximal of the distal end of the outer member to block fluid flow through the first lumen into the vessel and the side opening communicating with the first lumen for fluid flow;
  an inner member having a distal end and positioned within the first lumen of the outer member, the inner member having a second lumen terminating at the distal end of the inner member and having an opening for aspiration of particles proximally within the second lumen, wherein fluid from the first lumen enters the second lumen via the side opening and wherein when aspiration is on fluid is prevented from entering the vessel to thereby provide a closed system;
  a rotatable shaft positioned for rotational movement within the second lumen of the inner member and operatively connected to a motor; and
  a rotatable tip positioned at the distal region of the rotatable shaft and spaced from the distal end of the inner member and axially fixed with respect to the inner member to remain exposed during insertion and use of the atherectomy device, the rotatable tip rotatable by a motor to remove the deposits from the vessel for aspiration through the second lumen of the inner member.

In some embodiments, an aspiration hub is in communication with the second lumen and a fluid hub is in communication with the first lumen. The device can in some embodiments include a connector or cable extending from the housing for electrical connection to a wall outlet to power the device to effect rotation of the rotatable shaft and attached rotatable tip.

In accordance with another aspect of the present invention, an atherectomy device for removing deposits such as plaque from an interior of a vessel is provided comprising:
  a housing;
  a first hub positioned within the housing, the first hub including a fluid outlet and a fluid chamber;
  a second hub positioned within the housing and attached to the first hub, the second hub including an aspiration outlet and an aspiration chamber, the aspiration and fluid chamber axially aligned;
  an outer member extending from the housing and having a distal end, the outer member having a first lumen for fluid flow, a proximal end of the outer member positioned adjacent the fluid chamber;
  an inner member positioned within the first lumen of the outer member, the inner member having a second lumen terminating at the distal end of the inner member and having an opening for aspiration of particles proximally within the second lumen, a proximal end of the inner member positioned adjacent the aspiration chamber;
  a rotatable shaft positioned for rotational movement within the second lumen of the inner member and operatively connected to a motor; and
  a rotatable tip positioned at the distal region of the rotatable shaft and rotatable by a motor to remove the deposits from the vessel for aspiration through the second lumen of the inner member.

In some embodiments, the first hub is positioned distal of the second hub.

In some embodiments, a motor is positioned in the housing and a speed control switch selectively actuates the motor to a first speed to remove deposits and a second slower speed for proximal movement of the device over the guidewire to remove the device.

The device can include an augur mounted on the rotatable shaft. In some embodiments, the gap between the proximal end of the rotatable tip and the distalmost edge of the outer member creates a fixed spacing. In some embodiments, the inner member extends through the fluid chamber and is closed to the fluid chamber, i.e., does not fluidly communicate with the fluid chamber.

BRIEF DESCRIPTION OF THE DRAWINGS

Preferred embodiment(s) of the present disclosure are described herein with reference to the drawings wherein:

FIG. 2 is a longitudinal cross-sectional view of the distal portion of the atherectomy device of FIG. 1;

FIG. 3 is a view similar to FIG. 2 showing aspiration through the catheter:

FIG. 11A is a perspective view of the distal portion of another alternate embodiment of the atherectomy device of the present invention;

FIGS. 16A-16D show a method of use of the atherectomy device of FIG. 4 wherein:

FIG. 16A is a side view in partial cross-section of the guidewire being inserted through the vessel;

FIG. 16B is a side view in partial cross-section illustrating the rotating shaft and bit of the atherectomy device inserted over the guidewire;

FIG. 16C is a view similar to FIG. 16B showing rotation of the shaft to remove plaque; and FIG. 16D is a view similar to FIG. 16C showing further removal of plaque;

DETAILED DESCRIPTION OF PREFERRED EMBODIMENTS

Figure 1:
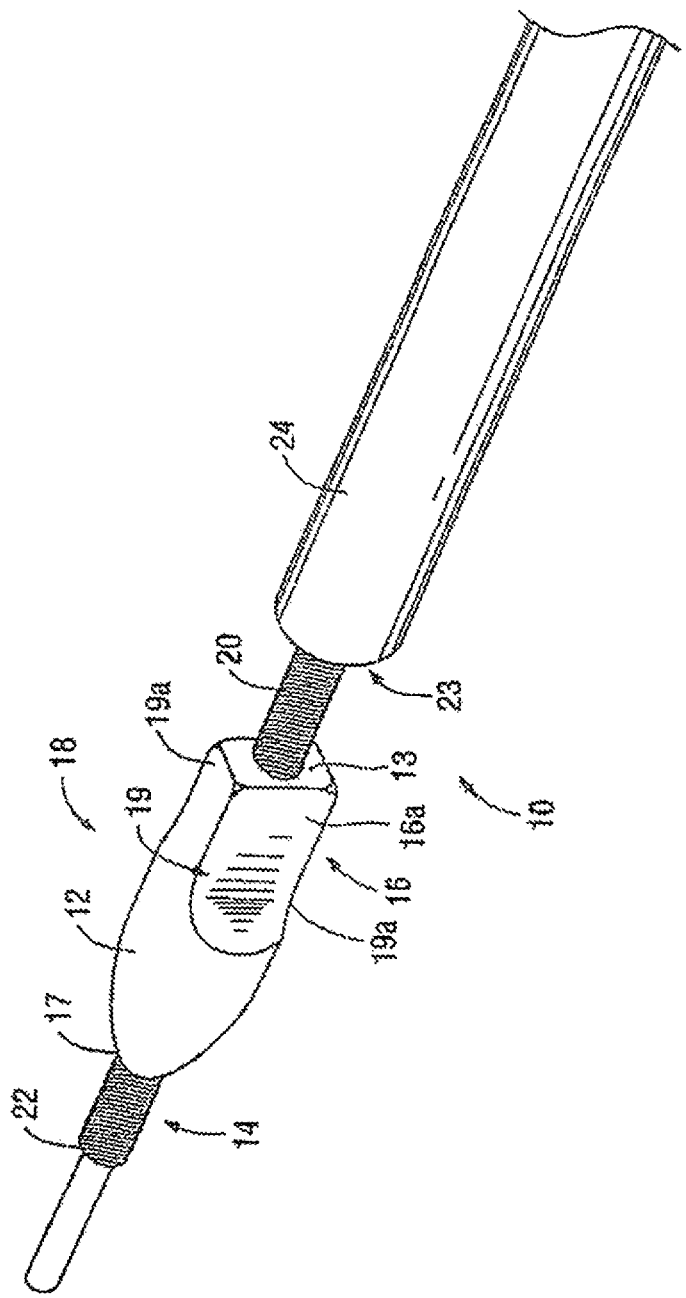
FIG. 1 is a perspective view of the distal portion of the atherectomy device of one embodiment of the present invention.

The present invention is directed to an atherectomy device designed for high speed rotation to remove plaque or other deposits on the inside wall of the vessel to widen the blood passageway therethrough. To achieve such rotation, the atherectomy tip is positioned at a distal portion of a flexible rotatable shaft that can be gas or electrically powered. The shaft rotates at high speed, typically between 100,000 and 200,000 rpm, causing the cutting or ablation surface of the tip to remove the plaque and deposits to which it comes into contact. The atherectomy device of the present invention has application in a variety of vessels such as the coronary arteries, peripheral vessels such as the tibial artery, femoral, and popliteal, and saphenous vein bypass grafts.

In order for the atherectomy tip to reach the vessel stenosis (obstruction) it is supported on a flexible shaft and inserted along with the flexible shaft through an introducer sheath and over a guidewire. More specifically, the introducer sheath is placed through a skin incision and into a vessel, e.g., the femoral artery in the patient's leg, to provide access to the target site. A guidewire is then inserted through the introducer sheath and advanced through the appropriate vessels to the target obstructed site, typically the coronary artery. The flexible shaft and attached atherectomy tip, extending from a catheter, are then inserted through the introducer sheath and threaded over the length of the guidewire to the target obstructed site. Actuation of the motor spins the shaft and tip so the cutting surface repeatedly comes into contact with the obstruction, e.g., plaque, to remove it from the vessel wall.

Details of the present invention will now be described with reference to the drawings wherein like reference numerals identify similar or like components throughout the several views.

Figure 24:
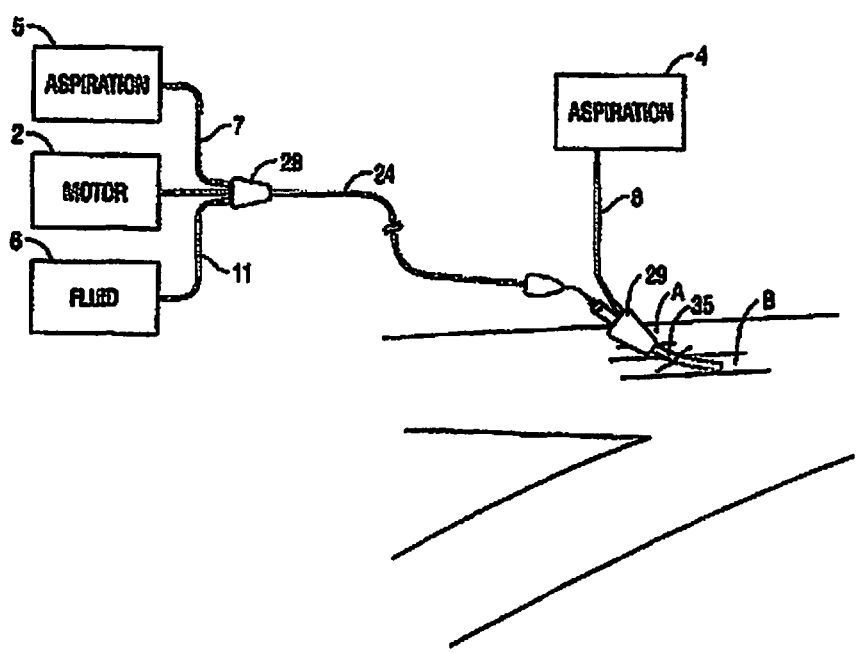
FIG. 24 is a schematic view illustrating the atherectomy system of one embodiment of the present invention.

FIG. 1 illustrates one embodiment of the atherectomy device of the present invention, designated generally by reference numeral 10. The entire device is shown in FIG. 24; the distal portion of the device is shown in FIGS. 1-3. The atherectomy tip or bit 12 of the device 10 is connected to a flexible rotatable inner shaft 20 such that rotation of the inner shaft 20 rotates the tip 12. The inner shaft 20 is positioned in outer tube or catheter 24. As shown, the tip 12 is connected at a distal region of the rotatable shaft 20, but shown spaced from a distalmost end 22 of the shaft 20. In an alternate embodiment, it is placed at the distalmost end of the flexible shaft 20. The flexible shaft 20 is electrically powered for high speed rotation to rotate the shaft 20 and tip 12 to break up plaque to treat stenosis of a vessel. A motor housing 2, shown schematically in FIG. 24, contains a motor mounted therein and a motor shaft. The atherectomy device 10 is operatively connected to the motor housing 2 as the flexible shaft 20 is connected to the motor such that activation of the motor rotates the shaft 20 of the device. A control knob can be provided to adjust the rotational speed of the shaft 20 and tip 12, and a window can be provided to visually display the speed. Shaft 20 and tip 12 can be disposable. In use, an introducer sheath or catheter 35 is inserted through an incision "A" in the patient's leg and through an incision in the femoral artery "B". The catheter or outer tube 24 with attached shaft 20 (positioned therein)

and tip 30 are introduced through the introducer sheath into the femoral artery "B", and advanced to the target artery, e.g., the coronary artery, to the treatment obstruction site. Note that a guidewire G extends through the shaft 20 and into the target artery so that the shaft 20 and tip 12 are inserted over the guidewire. FIG. 24 illustrates an exemplary introducer sheath 35.

The system in some embodiments further includes an aspiration (vacuum) source 5, shown schematically in FIG. 24, communicating with the catheter 24 to aspirate particles through the catheter 24 in the space (lumen 27) between the inner wall 24a of the catheter 24 and outer wall of shaft 20 (FIG. 2). Tubing 7 extends from the aspiration source 5 to communicate with the catheter 24 via catheter hub 28, and in some embodiments through a side arm (not shown) in catheter hub 28. The system in some embodiments can have an aspiration (vacuum) source 4 communicating via tubing 8 with the introducer sheath 35 via hub 29, and in some embodiments through a side port (not shown) in hub 29, to provide aspiration in the space between the inner wall of sheath 35 and the outer wall of catheter 24. Note the aspiration through the introducer sheath 35, if provided, can be in addition to the aspiration through catheter 24 or alternatively the sole source of aspiration in which instance aspiration source 5 would not be provided. The system can also include a fluid source 6 for delivering fluids to the vessel. Tubing 11 extends from the fluid source 6, through catheter hub 28, and in some embodiments through a side arm (not shown) in catheter hub 28, to communicate with the inner lumen 27 of catheter 24 or through the lumen of the shaft 20 so fluid can be introduced to the vessel.

It should be appreciated that the device 10 is shown inserted through the femoral artery by way of example as other vessels can be utilized for access, such as the radial artery. Also, the tip of the present invention can be used to remove plaque or other obstructions in a variety of vessels such as the coronary artery, the tibial artery, the superficial femoral, popliteal, saphenous vein bypass grafts and instent restenosis.

With reference to FIGS. 1-3, the first embodiment of the rotatable atherectomy tip of the present invention will now be described in more detail. Tip or burr 12 has a front (distal) portion (section) 14, a rear (proximal) portion (section) 16, and an intermediate portion (section) 18 between the front and rear portions 14 and 16. These portions vary in transverse cross-section as can be appreciated by the Figures. Thus, the front portion 14 can be defined for convenience as the area starting at the distalmost tip 17, forming a bullet nose configuration. The cross-section of the front portion 14 in one embodiment is substantially circular in configuration. The intermediate portion 18 can be considered as the region where the tip 12 transitions into the scalloped region 19. The cross-section of the intermediate portion 18 progressively changes from substantially circular, to an elongated shape having two substantially flat or linear opposing sidewalls 16a. This can also be viewed as removed material from the otherwise conical shape so that the distance between opposing linear walls 16a is less than the distance between opposing walls 19a.

Rear portion 16 can be considered to begin, for convenience, in the scalloped region 19, and terminate at the proximalmost edge 13 of tip 12. The rear portion 16 preferably has the same elongated cross-sectional dimension throughout its length, with substantially linear walls 16a separated by a distance less than the distance between opposing walls 19a.

The scalloped or narrowed section 19 is formed in both sides of the tip 12 to reduce the profile of the tip 12. These scalloped sections form the aforedescribed opposing substantially linear walls. By reducing the profile. i.e., the diameter and circumference, the atherectomy tip of the present invention could be inserted through smaller introducer sheaths than would otherwise be the case if the circumference increased with increasing diameter.

It should also be appreciated that the front, intermediate and rear portions/sections are designated for convenience and are not intended to require three separate segments connected together. Tip 12 can be, and is preferably, a monolithic piece.

Tip 12 has a proximal or rear opening 32 and a distal or front opening 34 connected by a lumen. The flexible shaft 20 extends through openings 32, 34 and the lumen and is attached to the tip 12. In some embodiments, the tip 12 is attached such that the shaft 20 extends through front opening 34 and extends a short distance distal of distalmost edge 17 of tip 12 as shown in FIG. 2. Shaft 20 has a lumen 25 dimensioned to receive a guidewire G to enable over the wire insertion of the atherectomy device 10.

The region of plaque removal is defined by the largest diameter region of the tip since the tip is rotating at high speeds and the plaque is cut or abraded only where the tip comes into contact with it. However, the sheath size required is determined by the largest circumference region of the tip. In some embodiments, the region of plaque removal can be further increased by altering the geometry and/or material of the tip 12 to create a wobbling effect which is described in more detail below.

As a result of the scalloped sections of the tip 12, as the diameter of tip 12 increases in one orientation, it decreases in the transverse orientation, enabling the circumference to remain constant. Since the diameter is reduced in one transverse orientation, the tip 12 can be introduced into an introducer sheath having an internal diameter slightly less than the largest diameter of the tip, since the sheath has room to deform because of the reduced regions, i.e., the scalloped sections, of the tip 12. In the prior art elliptical tip, the rounded symmetrical configuration leaves no room for the sheath to deform so the sheath size must exceed the largest diameter region. Thus, the tip 12 can fit into conventional introducer sheaths having an internal diameter less than the largest outer diameter of the tip 12. This can be achieved by the fact that the tip 12 can deform the internal walls of the sheath as it is inserted, by ovalizing the sheath. If the scalloped walls were not provided, the sheath would need to stretch, rather than ovalize to allow an oversized tip to pass.

Another way to view the tip 12 is that for a given catheter French size desired to be used by the surgeon, a larger atherectomy tip can be utilized if the atherectomy tip 12 of the present invention is selected instead of the prior art elliptical tip, thereby advantageously increasing the region of plaque removal to create a larger passageway in the vessel.

In alternate embodiments of the tip 12, longitudinal or elongated circular and oval cutting grooves could be provided to provide a roughened surface to cut or ablate the plaque as the tip is rotated. The grooves or indentations can be formed by laser cutting a series of grooves extending longitudinally within the interior of the tip stock. The tip is then ground to remove portions of the outer surface to partially communicate with the grooves, thereby creating indentations forming a roughened surface for contact with the plaque. The resulting formation is a series of elongated cutouts/indentations on the front and intermediate portions and oval shaped cutouts/indentations on the distal and intermediate portions. Another way contemplated to create the roughened surface is by blasting, e.g. sandblasting or grit blasting, the tip. The tip is held in a fixture and blasted at a certain pressure, thereby removing portions of the outer surface to create a roughened surface. Creation of a roughened surface by chemical etching is also contemplated. In an alternate embodiment, an abrasive coating, such as diamond particles, is applied to the tip. It should be appreciated that the foregoing roughened surfaces, abrasive coating, etc. can be applied to any of the atherectomy tips described herein.

Figure 9:
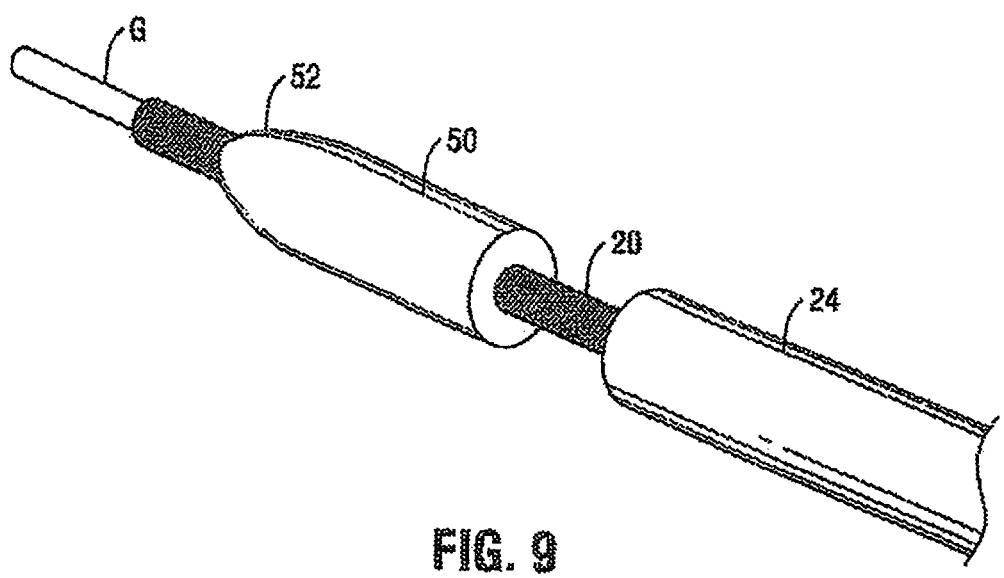
FIG. 9 is a perspective view of a distal portion of another alternate embodiment of the atherectomy device of the present invention.

FIG. 9 illustrates an alternate embodiment of the atherectomy tip. In this embodiment, the tip, designated generally by reference numeral 50, does not have scalloped sections but instead is substantially cylindrical in configuration along its length except for the bullet nose tip 52. That is, it is circular in transverse cross-section throughout its length. In all other respects, the atherectomy device of FIG. 9 is the same as FIG. 1, i.e., includes rotatable shaft 20 extending beyond the atherectomy tip, catheter 24, etc., so for brevity these components will not be discussed herein since the discussion of these components with respect to FIG. 1 are fully applicable to the embodiment of FIG. 9.

Figure 3A:
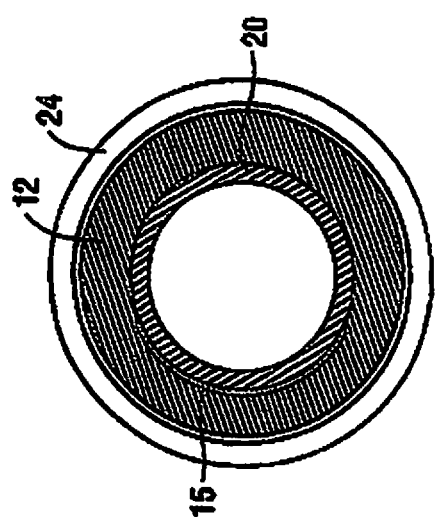
FIG. 3A is a transverse cross-sectional view of the tip of FIG. 1.

In some embodiments, the atherectomy tip is symmetrical. In alternate embodiments, the outer geometry of the tip is symmetrical, however, an inner portion of one side of the tip is carved out or removed to create an imbalance resulting in an offset center of mass. This results in wobbling of the tip during high speed rotation which in turn enables a spinning diameter to exceed the cross-sectional dimension of the tip. In this manner, the tip can be used to remove plaque in a wider transverse area. This is shown in FIG. 3A with material removed from one side of the tip 12 to create a cutout or removed material section 15.

Removing material from one side of the tip is one way to achieve this wobbling effect. Another way is through the tip itself being composed of materials of different density, either the same material of different densities or different materials of a differing density such as in FIG. 10B. Such materials utilized can include by way of example platinum and aluminum. These two ways of achieving the wobbling effect are also discussed below in conjunction with the two piece tip.

Referring back to FIGS. 1-3, as shown, the tip 12 is fixed to the rotatable shaft 20 and positioned distal of the distalmost end of the catheter 24. The shaft 20 is axially fixed within catheter (outer member or outer tube) 24 but can rotate with respect to the catheter 24. Such fixation is described below in conjunction with the embodiment of FIG. 12A. The tip 12 therefore remains distal of the distal opening 23 in the catheter 24 to maintain the gap e.g., a fixed gap between the proximal edge 13 of the tip 12 and the opening 23 so particles can be aspirated through the opening 23 and lumen 27 of the catheter 24.

Figure 11B:
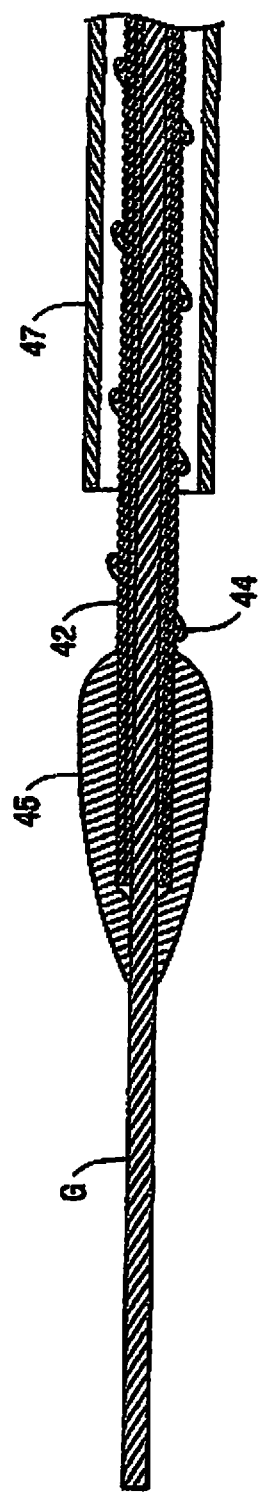
FIG. 11B is a longitudinal cross-sectional view of the device of FIG. 11A.

In the alternate embodiment of FIGS. 11A and 11B, device 40 includes a rotatable shaft 42 having an auger or series of threads 44 proximal of tip or bit 45. The auger 44 is positioned on the region of the shaft 42 proximal of the proximal edge 49 of tip 45 and extends along a length of the shaft 42 within catheter (outer tube) 47. These threads 44 function as an Archimedes screw. i.e., a screw pump, to remove the plaque. That is, as the shaft 42 is rotated in the same manner as shaft 20, the screw's helical surface scoops particles and directs the particles proximally (rearwardly) along the shaft 42 through the lumen of catheter 47. In all other respects, device 40 is identical to device 10. The auger 44 can be used in addition to an aspiration pump for aspirating particles into the opening 48 of catheter 47 (as in the embodiment of FIGS. 1-3) or alternatively used as a substitute so it provides the sole mechanism for aspirating particles through the lumen of the catheter 47. The auger 44 can extend along the entire length or along a partial length of the shaft 20. The auger 44 for removing particles can be used with any of the atherectomy devices disclosed herein.

FIGS. 4-8, 10A and 10B illustrate alternate embodiments of the atherectomy tip of the present invention wherein the tip is composed of two separated components. More particularly, in the embodiment of FIGS. 4-8 and 10A, the tip 60 of atherectomy device 61 has a first component 62 and a second component 64. Tip 60 is mounted on rotatable shaft 70 (similar to shaft 20) at a position spaced proximally from the distalmost edge 72 of the shaft 70 so that a distal portion of the shaft 70 extends slightly distally of the distalmost edge 65 of tip 60. Shaft 70 is rotatably mounted within lumen 82 of catheter 80 but axially fixed within catheter 80 to create a fixed gap between the tip 60 and catheter 80. The shaft 70 has a lumen for insertion over a guidewire G.

With reference to FIGS. 5-8 and 10A, tip component 62 has a cutout or removed material portion 66 to reduce the amount of material of the tip. Tip component 64 does not have such cutout. In this manner, due to the material imbalance which creates an offset center of mass, the tip 60 will wobble when rotated to remove plaque in an area greater than a transverse dimension of the tip 60.

Figure 10A:
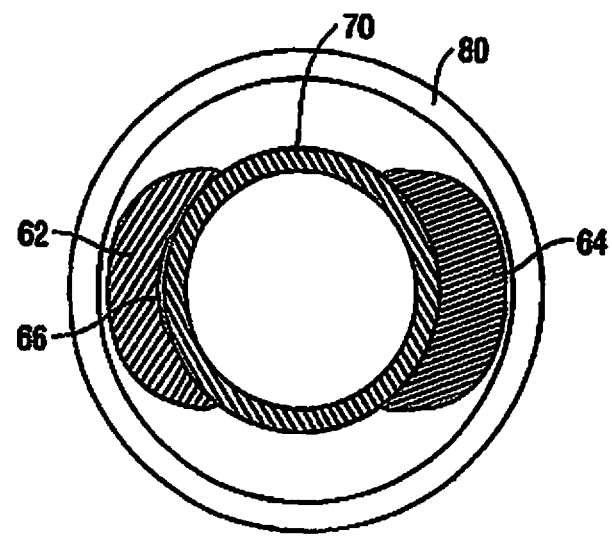
FIG. 10A is a transverse cross-sectional view of the bit of FIG. 4.
Figure 10B:
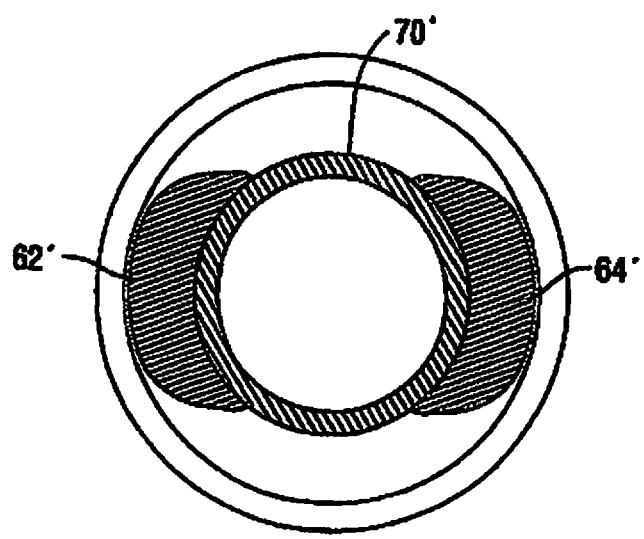
FIG. 10B is a view similar to FIG. 10A showing an alternate embodiment of the atherectomy bit of the present invention.

In the embodiment of FIG. 10B, the two tip components 62', 64' have different densities to achieve the wobbling effect. The tip components 62', 64' are attached to rotatable shaft 70' which is fixed to catheter (outer member) 80'. Shaft 70' and catheter 80' are identical to the aforedescribed shafts 20 and 70 and catheters (outer member) 24 and 80.

Figure 12A:
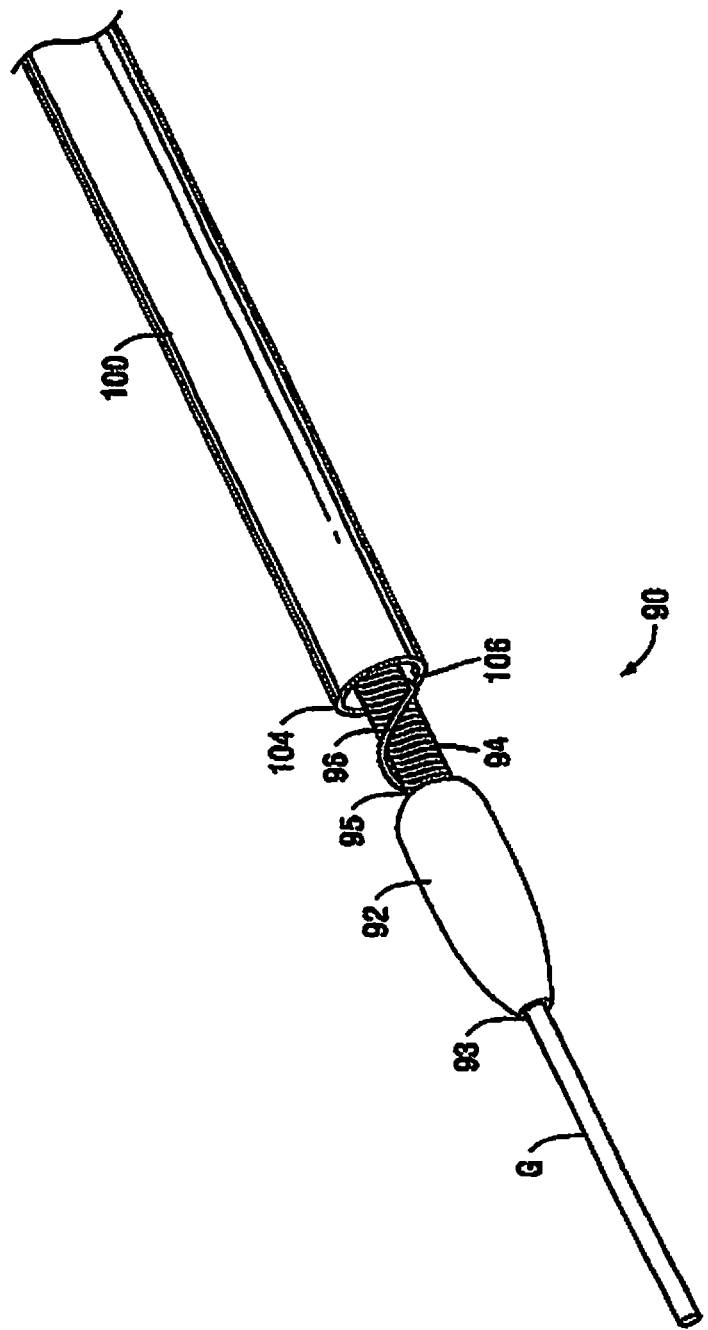
FIG. 12A is a perspective view of the distal portion of another alternate embodiment of the atherectomy device of the present invention.
Figure 12B:
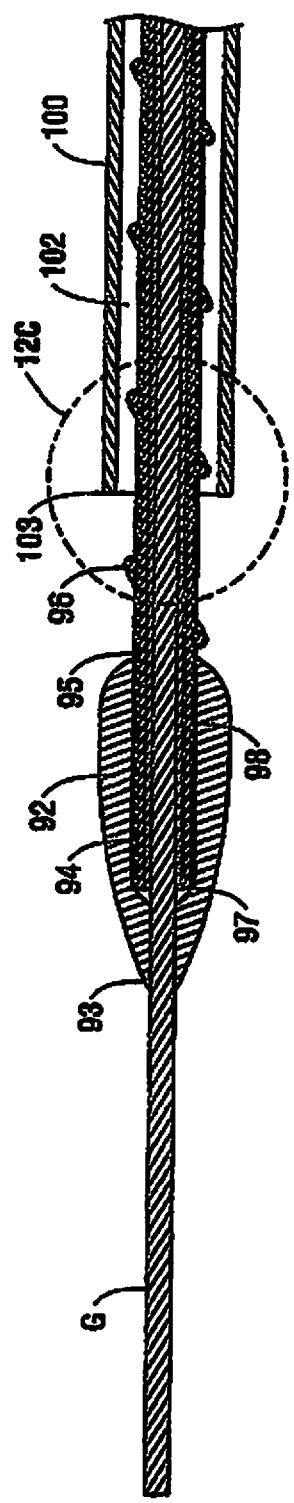
FIG. 12B is a longitudinal cross-sectional view of the atherectomy device of FIG. 12A.
Figure 12C:
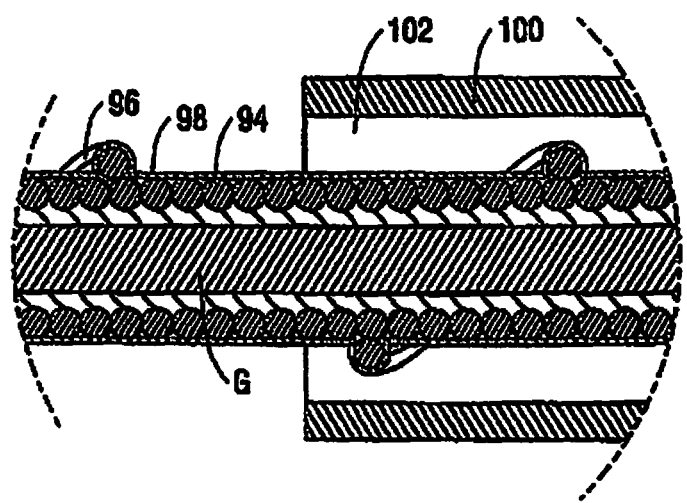
FIG. 12C is a close up view of the area of detail identified in FIG. 12B.

FIGS. 12A-12C illustrate an alternate embodiment of the atherectomy device. The device 90 includes a rotatable atherectomy tip or bit 92 similar in configuration to tip 50 of FIG. 9. Rotatable tip 92 has a lumen between its proximal and distal openings through which flexible rotatable shaft 94 partially extends, terminating proximal of the distal opening of tip 92. That is, tip 92 is attached to rotatable shaft 94 at a distal end so the shaft 92 does not extend beyond the distalmost end 93 of tip 92. Stated another away, a distal portion of the tip 92 extends distally of the distalmost end 97 of shaft 94. Alternatively, the tip 92 can be attached to the flexible shaft spaced proximally of the distalmost end of the shaft 94 so a portion of the shaft 94 extends distally of the distalmost tip 93 of tip 92 in the same manner as in the embodiments of FIGS. 1 and 9. Shaft 94, like shaft 20, has a lumen dimensioned to receive a guidewire G to enable over the wire insertion of the atherectomy device 90.

Rotatable shaft 94 has an auger or series of threads 96 proximal of tip or bit 92. The auger 96 is attached to the shaft 94, e.g., by welding at several regions, and is positioned on the region of the shaft 94 proximal of the proximalmost edge 95 of tip 92 and extends along a length of the shaft 94 within outer tube or catheter 100. These threads function as an Archimedes screw. i.e., a screw pump, to remove the plaque in the same manner as auger 44 described above. That is, as the shaft 94 is rotated, the screw's helical surface scoops particles and directs the particles proximally (rearwardly) through opening 104 and along the shaft 94 through the lumen 102 of catheter 100. The auger 96 can be used in addition to an aspiration pump for aspirating particles into the distal opening of catheter 100 (as in the embodiment of FIGS. 1-3) or alternatively used as a substitute so it provides the sole mechanism for aspirating particles through the lumen 102 of the catheter 100. The auger 96 has a portion exposed between the distal end 103 of catheter 100 and the proximal end 95 of shaft 94 as shown.

A coating 98 can be provided over the rotatable shaft 92, including over the auger 96. The coating covers at least the distal portion of the rotatable shaft 92, i.e., the portion exposed from the catheter 100. That is, the coating 98 can start just proximally of the tip 92 and extend to cover only the portion of the shaft 92 between the proximal end 95 of tip 92 and the distal end 103 of catheter 100. Alternatively, the coating 98 can cover other, regions of the shaft 94, and in some embodiments, can cover the entire length of the shaft 92 including the region of the shaft 94 within tip 92 as shown in FIG. 12B. Examples of coatings that can be utilized include PTFE or PET, although other materials are also contemplated. The coating covers the coils of the rotatable shaft 92 so they do not pinch the vessel. The coating can further function to help hold the auger 96 close to the rotatable shaft 94. It should be appreciated that the coating can be utilized with the other embodiments described herein.

Figure 13A:
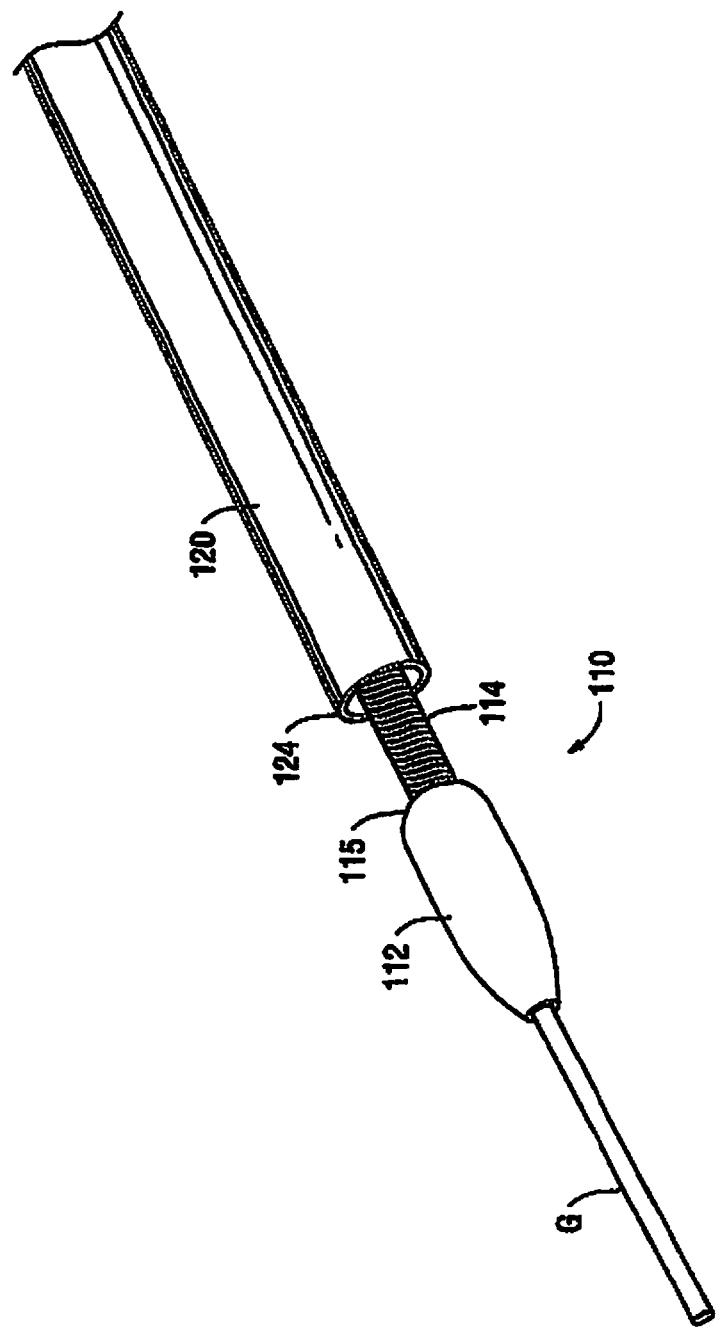
FIG. 13A is a perspective view of the distal portion of another alternate embodiment of the atherectomy device of the present invention.
Figure 13B:
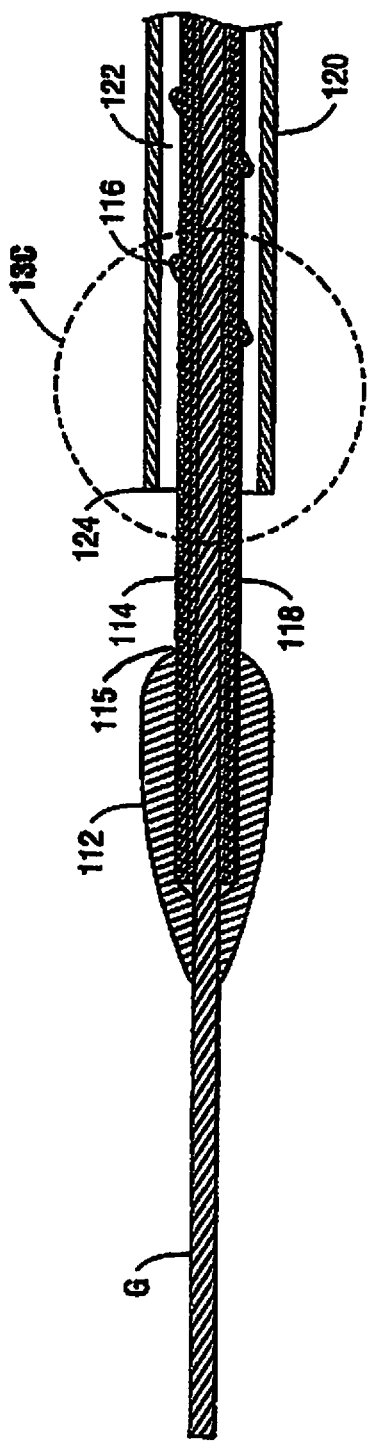
FIG. 13B is a longitudinal cross-sectional view of the atherectomy device of FIG. 13A.
Figure 13C:
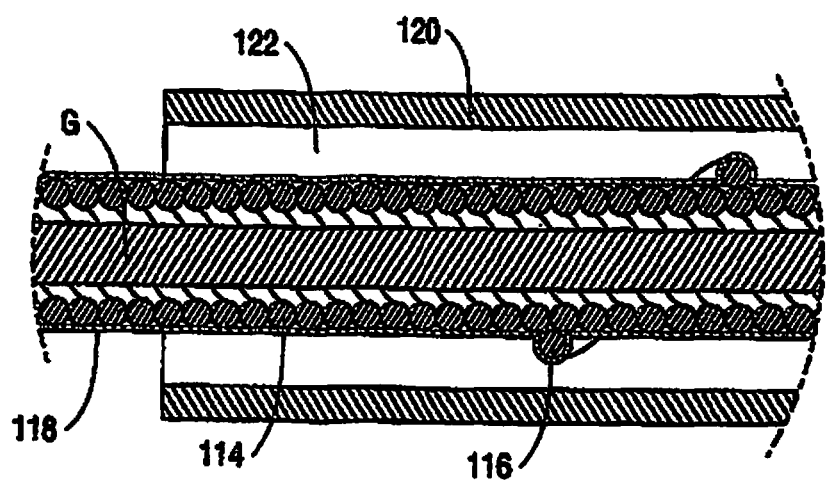
FIG. 13C is a close up view of the area of detail identified in FIG. 13B.

In the embodiment of FIGS. 12A-12C, the auger 96 is exposed between the distal end 103 of catheter 100 and the proximal end of the tip (bit) 92. In the alternate embodiment of FIGS. 13A-13C, the auger 116 of atherectomy device 100 is not exposed between the distal end 124 or distalmost edge of catheter 120 and the proximal end 115 or edge of the tip 112. That is, the auger 116 terminates at a distal end within the catheter 120. In all other respects, device 120 is identical to device 90 of FIGS. 12A-12C.

A coating 118 can be provided over the rotatable shaft 114, including over the auger 116 in the same manner as shaft 94 described above. The coating 118, as in coating 98, covers at least the distal portion of the rotatable shaft 114. i.e., the portion exposed from the catheter 120—starting just proximally of the tip 112 and extending to cover only the portion between the tip 112 and the distal end 124 of catheter 120. Alternatively, the coating 118 can cover other regions of the shaft 114, and in some embodiments, can cover the entire length of the shaft 114.

As discussed above, the catheters of the various embodiments disclosed herein are axially (and rotatably) fixed with respect to the motor and motor housing. The shafts are rotatably mounted to the motor but axially fixed with respect to the motor (and motor housing). In this manner, actuation of the motor rotates the shaft and attached atherectomy tip while the position of the tip with respect to the catheter remains fixed since the catheter (and rotatable shaft) are axially fixed, i.e., do not move in an axial direction. In this manner, a gap, e.g., a fixed gap, between the atherectomy tip and the catheter is maintained to enable aspiration of particles into the distal end of the catheter, either by the rotating auger or a vacuum, or the combination of both the auger and vacuum, as described herein.

Figure 14:
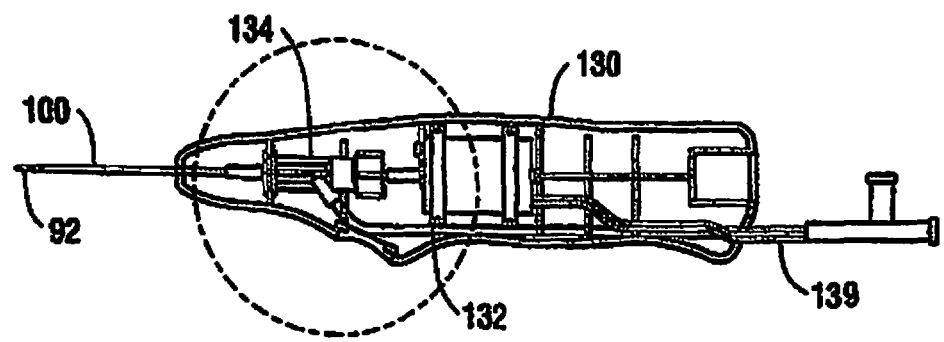
FIG. 14 is a side view of the housing of the atherectomy device of FIG. 12A, with a housing half removed to show internal components.
Figure 15:
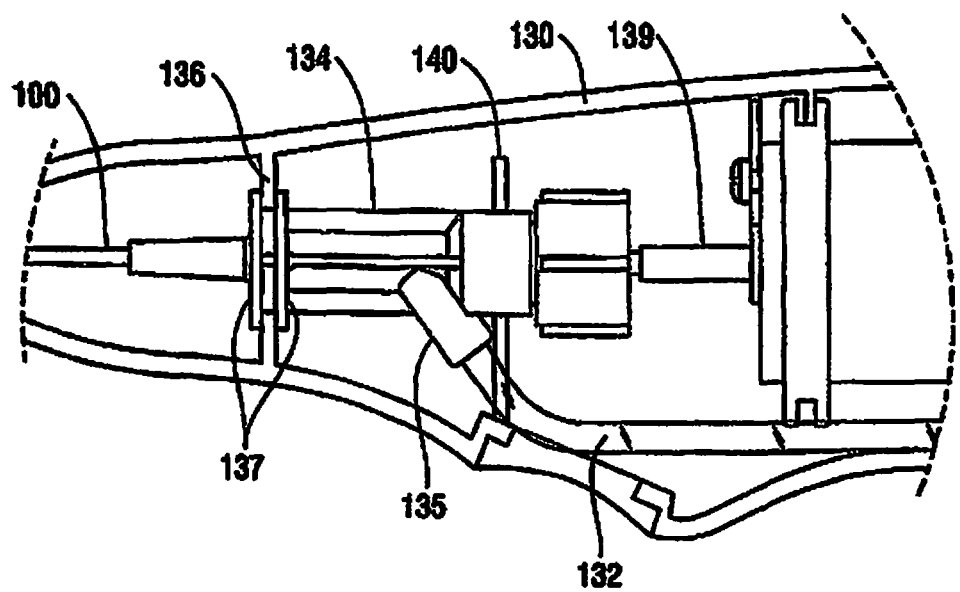
FIG. 15 is an enlarged view of the area of detail identified in FIG. 14.

FIGS. 14 and 15 illustrate an exemplary mounting of the rotatable shaft to the motor. The mounting is shown for the atherectomy device 90 of FIG. 12A, it being understood that the atherectomy devices of the other embodiments described herein can be mounted in the same fashion. As shown, handle or motor housing 130 has an internal rib 136 affixed between rings 137 of hub 134 of atherectomy device 90. Catheter 100 is fixedly mounted to the hub 134 and extends distally thereof. A proximal rib 140 within housing 130 receives a more proximal portion of hub 134 and provides additional support. Thus, hub 134 and attached catheter 100 are fixedly mounted within the motor housing 130. The rotatable shaft 94, extending through hub 134, is unattached to catheter 100 and rotatably operatively connected to motor shaft. The shaft 94 is axially fixed.

A series of wires 139 extend from the motor and terminate in a plug for powering the motor. Aspiration tube 132 extends from side port 135 of hub 134 to remove aspirated particles.

FIGS. 17-23C illustrate an alternate embodiment of the atherectomy device of the present invention. The atherectomy device, designated generally by reference numeral 150, has a dual lumen catheter 152, a rotatable shaft 153 positioned within the catheter 152, a rotatable bit or burr 154 attached to the rotatable shaft 153, a handle 158 and a hub region 156 contained within the handle 158 for infusion and aspiration of particles.

Turning first to catheter 152, catheter 152 includes an outer component or member (catheter) 160 and an inner component or member (catheter) 162. In a preferred embodiment, the inner member 162 includes a proximal inner member 164 and a distal inner member 166 which are spaced apart, i.e., the proximal end of the distal inner member 166 is spaced distally from the distal end of the proximal inner member 164 to create a gap 168. In one embodiment, the two members 164, 166 can be formed from a single catheter (member) which is cut and separated into the two components. In alternate embodiments, the inner member can comprise two separately formed catheters. In other embodiments, the inner member can be made of a single member (catheter) with an opening formed in the side wall to align with the side opening of the outer member 160 rather than the catheter separated into two components to provide a gap.

The proximal inner member 164 includes a lumen 170 and the distal inner member 166 includes a lumen 174 axially aligned with lumen 170. Aspiration occurs though lumens 174, 170 due to rotation of the augur 186 positioned (mounted) over and connected to the rotatable shaft 153 described below. The distal inner member 166 terminates in a distal opening 176 which is open to the body lumen of the patient. Opening 176, and thus distalmost edge 177 of distal inner member 166, is spaced proximally from bit 154 to provide a gap having a distance D1 from the proximalmost edge 154a of the bit 154 and the distal edge 177. In some embodiments by way of example, distance D1 can range from about 0.125 inches to about 2 inches and preferably between about 0.60 inches to about 0.90 inches and more preferably about 0.75 inches. In preferred embodiments, the gap range is selected so the augur does not extend distally beyond the distal inner member 166. In other embodiments, the augur can extend beyond the distal inner member to be exposed. Other distances are also contemplated. As the augur 186 is rotated as described below, particles removed from the vessel by the bit 154 are aspirated rearwardly (proximally) through the lumens 174, 170 of the inner member and through the hub region 156 and out through an aspiration tube. The inner member 166 and preferably also inner member 164 are fixed axially so that the distance D1 between the distalmost end 177 of the distal inner member 166 and the bit 154 is fixed. i.e., remains constant during insertion and use of atherectomy device 150. The distal inner member 166 extends distally for a distance beyond the distalmost end 179 of the outer member 160. The proximal inner member 164 extends into and terminates in the hub region. Note the term fixed axially as used herein throughout the application encompasses no movement at all as well as encompasses "substantially fixed axially" wherein only insignificant (negligible) axial movement occurs.

The outer member 160 is coaxial with the inner member 162 and has a lumen 180 to receive the inner member 162 therein. That is, both the proximal inner member 164 and distal inner member 166 are coaxially received within lumen 180. Outer member 160 is fixed axially with respect to the inner member 162 and thus the hub region 156 and housing 158. Lumen 180 enables flow of fluid from a fluid source into the proximal inner member 164. More specifically, outer member 160 has a side opening 165 radially aligned with the gap 168 between the proximal inner member 164 and distal inner member 166. End wall 167 of outer member 160 provides a terminal end wall of lumen 180 to ensure infusion through the side opening 165. Thus, fluid infusion in a distal direction passes through the side opening 165 and into lumen 170 of proximal inner member 164 as flow terminates at end wall 167 and is redirected into lumen 170 and directed rearwardly by the augur 186. The infusion of fluid functions to cool the device 150 during use, without affecting aspiration as infusion occurs from the region of the side opening 165 back, spaced from the distal region of the device 150. The fluid infusion functions as a safety feature if the system gets blocked which could lead to device failure if the system runs dry. That is, during high speed rotation of the shaft 153, if there is a blockage and the shaft 153 continues to spin and heat up, the system can fail if the shaft 152 is not properly lubricated. The fluid flow in the proximal direction dissipates heat. The heat dissipation also facilitates gripping of the catheter 152 by the clinician by preventing the catheter 152 from getting too warm. The outer member 160 terminates at proximal end 163 in hub region 156. The outer member 160 terminates at distal end 179 spaced proximally from the distal end of the distal inner member 166 of inner member 162, which in some embodiments can be about 30 centimeters from the distal end, but other distances are also contemplated.

Note that fluid flow proximally in lumen 170 of proximal inner member 164 is enhanced by rotation of the augur 186. During rotation of the rotatable shaft 153 and augur 186, fluid does not flow into the body lumen of the patient because it is directed rearwardly by the augur 186, thus providing a closed system when the device is in use. Stated another way, injection of fluid into the body lumen (vessel) is prevented when the motor is actuated and aspiration occurs (is turned on) to provide a closed fluid system. The fluid can be infused continuously, if desired, when the device is turned on.

In one embodiment, the outer member 160 is formed by two catheters 160a, 160b, formed by various methods including for example gluing the two catheters together or by taking a piece of plastic and heating it so it melts the two catheters. The catheters can be made of variable materials such as Pebax, nylon, polyimide or other materials. The catheter 160b is then glued to the inner member 162, e.g., distal inner member 166. Note in this embodiment, the catheter 160b closes off the lumen 180 at proximal end wall 167. In an alternate embodiment, the distal inner member (catheter) and the outer member (catheter) are formed as one piece, as a bumped catheter, and the proximal inner member is a separate piece.

Figure 18A:
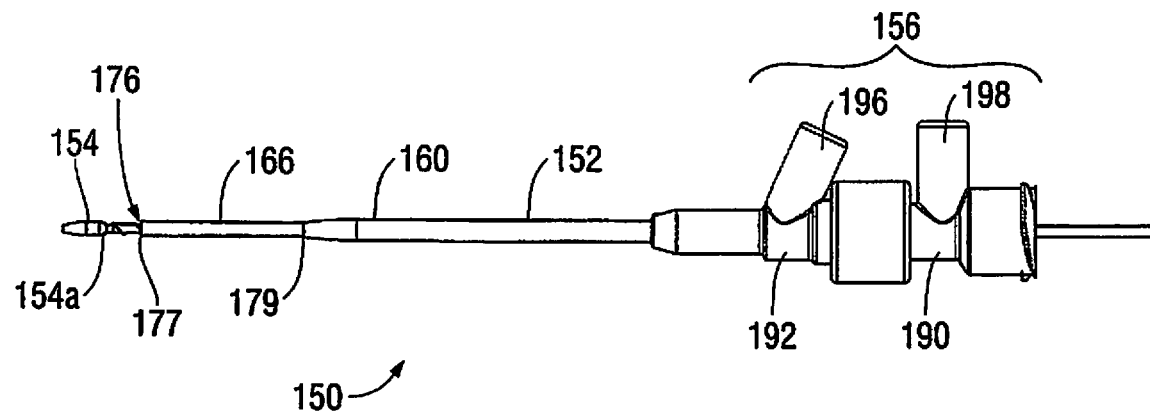
FIG. 18A is a side view of the atherectomy device of FIG. 17 with the housing and its internal components removed to show the hub portion.
Figure 18B:
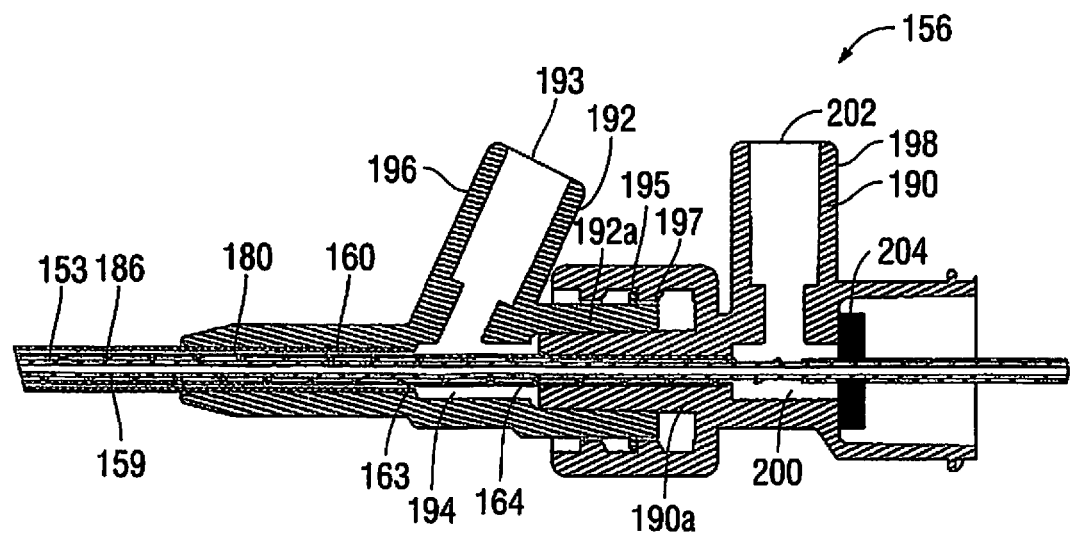
FIG. 18B is a longitudinal cross-sectional view of the hub portion of the atherectomy device of FIG. 17.
Figure 19:
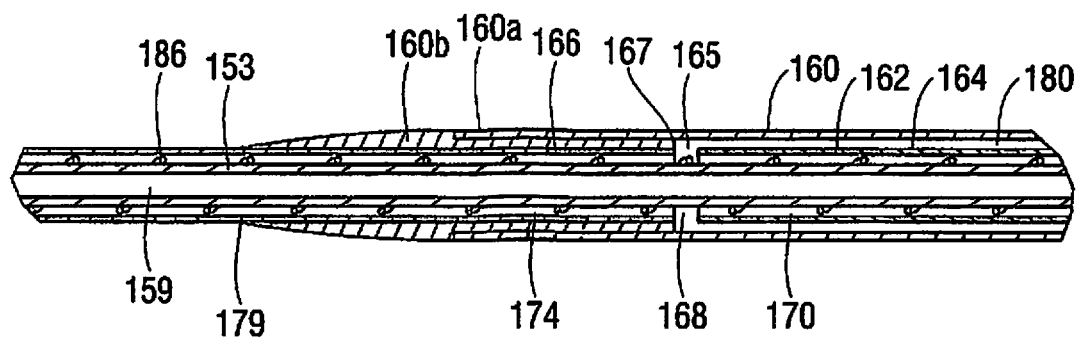
FIG. 19 is a longitudinal cross-sectional view of the catheter/shaft portion of the atherectomy device of FIG. 17.
Figure 20:
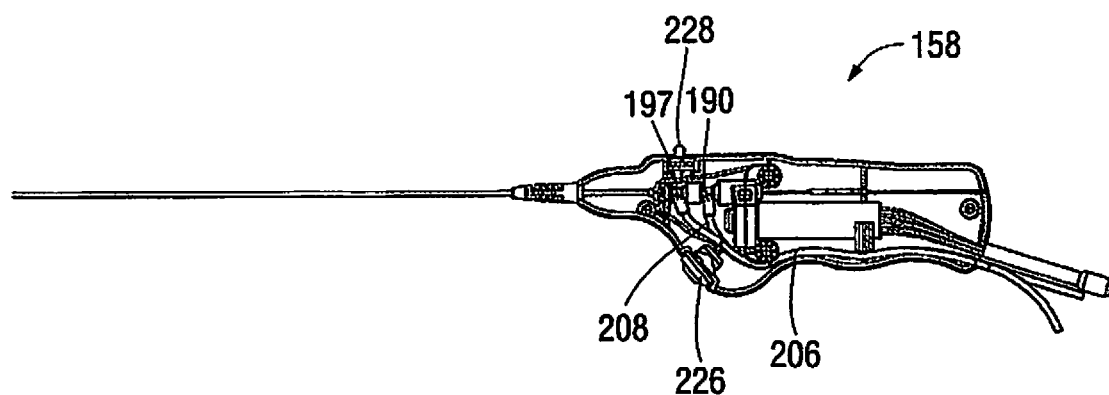
FIG. 20 is a side view of the handle portion of the atherectomy device of FIG. 17 with a portion of the housing removed to show internal components.
Figure 21A:
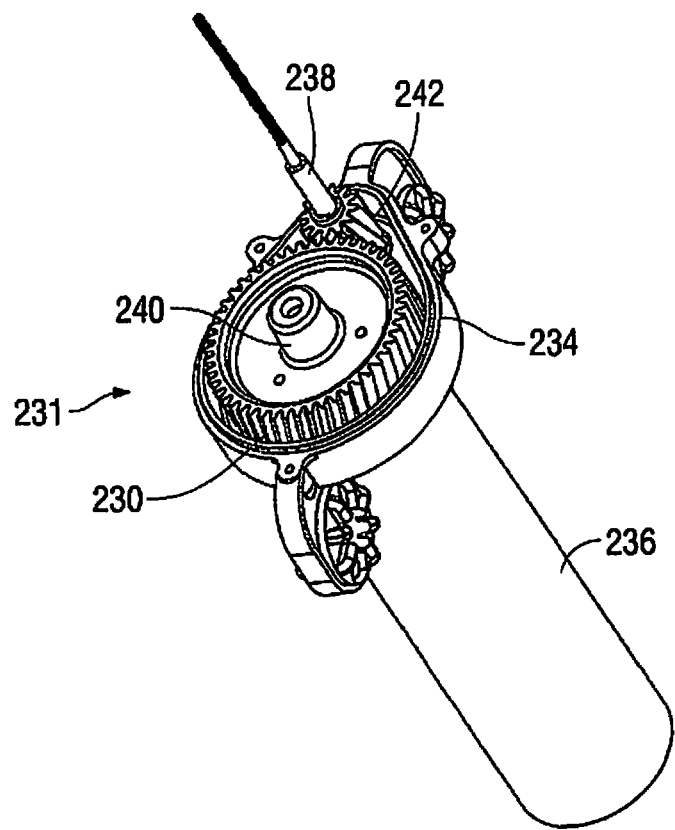
FIGS. 21A-21C illustrate the gear assembly of the handle portion of FIG. 20.
Figure 21B:
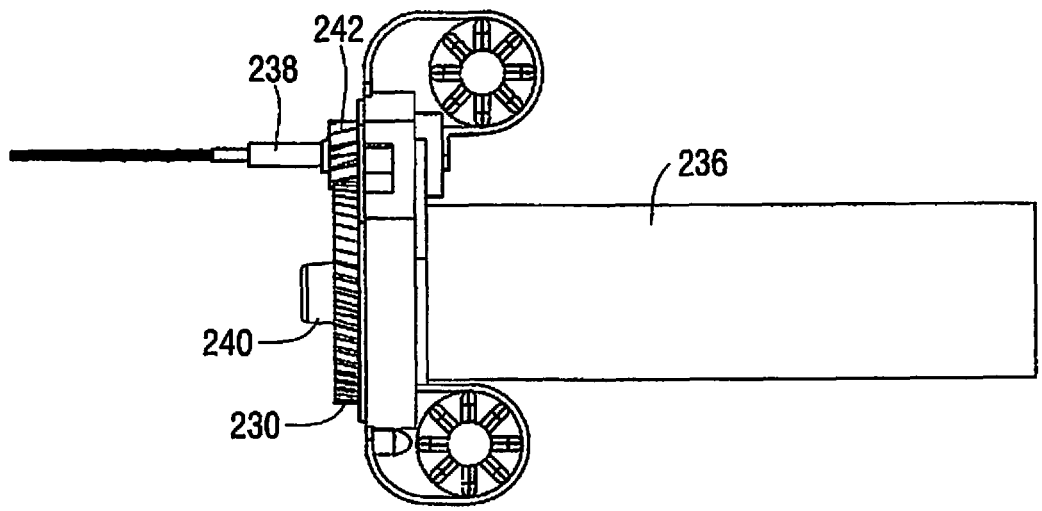
Figure 21C:
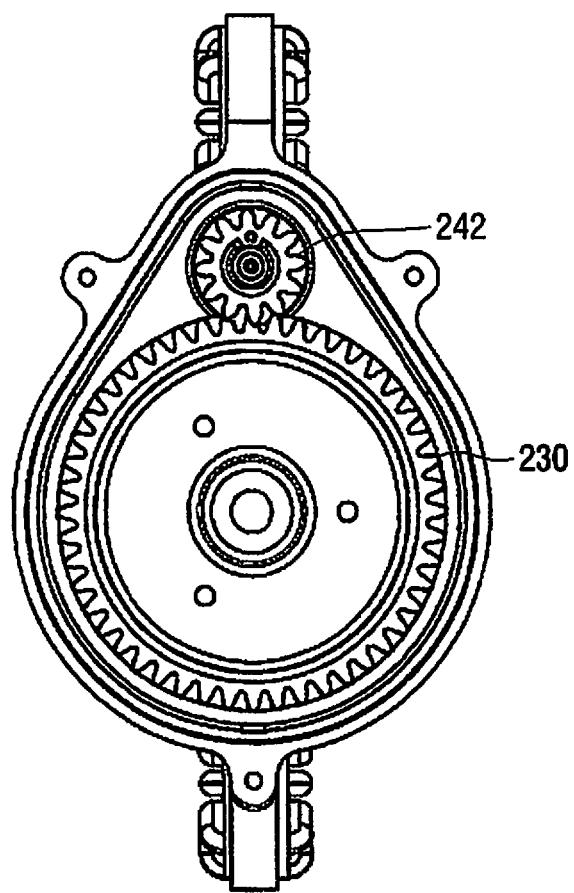
Figure 22A:
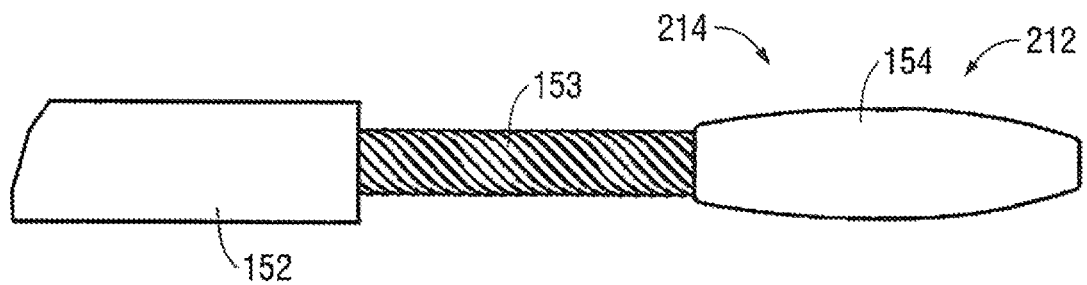
FIG. 22A is a side view of the distal region of the atherectomy device of FIG. 17.
Figure 22B:
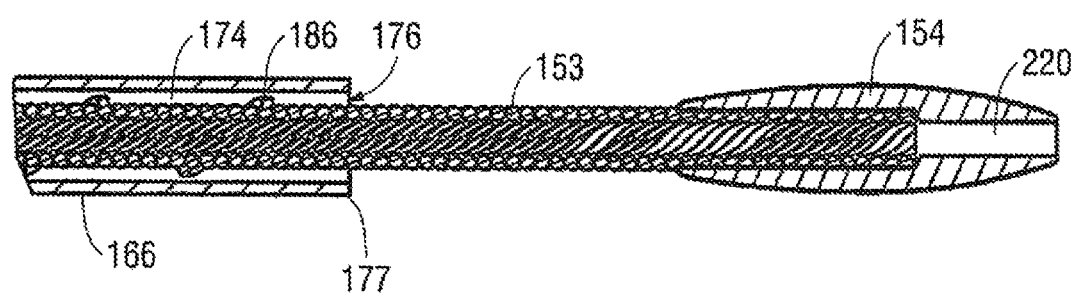
FIG. 22B is a longitudinal cross-sectional view of the distal region of the atherectomy device of FIG. 17.
Figure 22C:
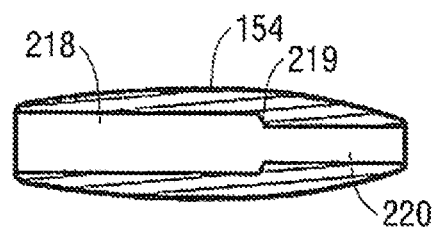
FIG. 22C is cross-sectional view of the atherectomy tip of FIG. 22A with the roatatable shaft removed.

Turning now to hub region 158, and with particular reference to FIGS. 18B and 20, an aspiration hub 190 and an infusion hub 192 are provided. The hubs 190, 192 are positioned within handle (housing) 158. Infusion hub 192 in this embodiment is positioned distal of aspiration hub 190 and has a side port 196, preferably positioned at an acute angle to the longitudinal axis of the hub 192 as shown, although other angles are also contemplated. Infusion hub 192 has an outer thread 195 to receive internal thread 197 of aspiration hub 190 to threadedly connect the two hubs 190, 192. As shown, outer thread 195 is formed on a proximal extension 192a of infusion hub 192 and inner thread 197 is formed on distal extension 190a of aspiration hub 190. Fluid infusion through opening 193 of hub 192 (via tubing 206 which connects to an external fluid source) enters chamber 194 and advances into lumen 180 of outer member 160 as outer member 160 has a proximal opening communicating with chamber 194 and continues in the space between the inner wall of the outer member 160 and the outer wall of inner member 162 (proximal inner member 164).

Aspiration hub 190 has a side port 198, preferably positioned at a right angle to the longitudinal axis of the hub 190 as shown, although other angles for the side port 198 are also contemplated. Aspiration hub 190 includes an internal chamber 200 in communication with the lumen 170 of proximal inner member 164 as the proximal opening of proximal inner member 164 (which extends proximal of outer member 160 and its proximal opening) communicates with the chamber 200 so that particles aspirated by the augur 186 (and aided by rearward fluid flow) move into chamber 200 and out from opening 202 of side port 198 and into tubing 208 communicating with an external collection chamber. A valve 204 is positioned proximal of chamber 200 to prevent back flow.

As noted above, rotatable shaft 153 has an augur 186 attached to its outer surface for aspiration. Rotatable shaft 153 is fixed axially with respect to the inner and outer members 162, 160 and housing 158, however, it is rotatable with respect to the inner and outer members 162, 160 and housing 158. The rotatable shaft 153 is positioned within the lumen 170 and 174 of the inner members 164, 166 and extends distally of distalmost edge 177 of distal inner member 166 (see e.g., FIG. 22B) so that bit 154 attached to shaft 153 is spaced a sufficient distance from the opening 176 of distal inner member 166 to facilitate aspiration of particles removed by the bit 154. As noted above this distance or gap remains constant during insertion and use of the device 150. In this embodiment, the augur 186 extends distally of distalmost edge 177 as it is exposed in the gap (see distance D1 of FIG. 18A) between the bit 154 and the distal inner member 166 of the inner member 160 of the catheter 152. In other embodiments, the augur terminates proximal of the gap so it is not exposed from the catheter 152. The augur 186 terminates proximally in hub region 156 within aspiration chamber 200. The augur 186 is similar to the augur described above with respect to the other embodiments. The rotatable shaft 153 has a lumen 159 for receipt of a guidewire for over the wire insertion of the atherectomy device 150. The guidewire extends through an opening at a proximal end of the handle 158, spaced from the aspiration and infusion side ports through which the aspiration and infusion tubes extend. A disposal bag (not shown) is attached to the aspiration tube.

Figure 23A:
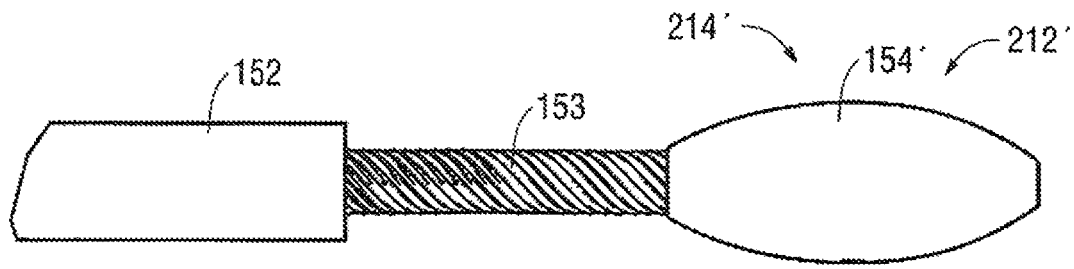
FIG. 23A is a side view of a distal region of the atherectomy device in accordance with an alternate embodiment.
Figure 23B:
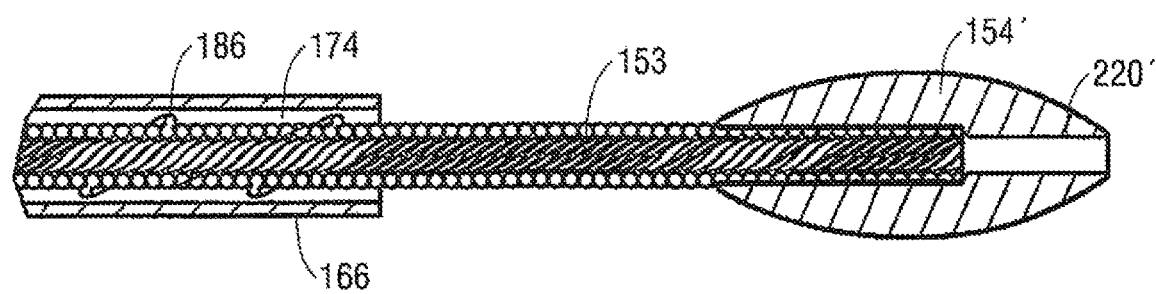
FIG. 23B is a longitudinal cross-sectional view of the distal region of FIG. 23A.
Figure 23C:
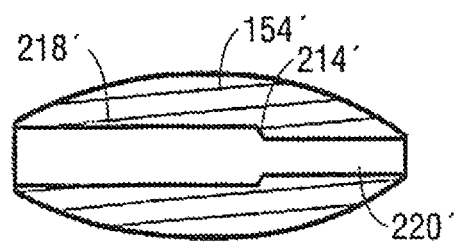
FIG. 23C is cross-sectional view of the atherectomy tip of FIG. 23A with the rotatable shaft removed.

Bit 154, as shown in FIGS. 18A and 22A-22C, has a football like shape with a distal region 212 curving distally inwardly to a reduced diameter and a proximal region 214 curving proximally inwardly to a reduced diameter. A substantially flat intermediate region can be provided between the two regions 214, 212. This shape provides a smooth less traumatic surface as the smooth transition avoids an edge or shoulder that could cause trauma to the vessel as the bit 154 is moved axially either distal or proximally. Also, due to the smooth surface and uniformity (symmetry), the movement feels the same to the user whether moving the device distally or proximally. The bit 154 has a proximal lumen 218 to receive the rotatable shaft 153 for mounting to the shaft 153 and a distal lumen 220 in communication with lumen 218. In a preferred embodiment, the diameter of the distal lumen 220 is less than the diameter of the proximal lumen 218. The proximal lumen 218 provides for passage and attachment of shaft 153 as it abuts shoulder 219 which is at the transition between lumens 218, 220; the distal lumen 220 provides for passage of a guidewire which passes though the lumen 159 in shaft 153. This enables the bit 154 to be inserted over a guidewire as the guidewire extends through the rotatable shaft 153 and bit 154. FIGS. 23A-23C show an embodiment similar to FIGS. 22A-22C, but having a larger bit size. Bit 154' has lumens 218', 220' and these lumens 218', 220' can have the same internal diameter as lumens 218, 220, respectively, of bit 154. However, bit 154' has a larger cross-sectional diameter than bit 154 in the distal region 212', proximal region 214' region and intermediate region between the proximal and distal regions 214', 212'. As in bit 154, distal region 212' curves distally inwardly to a reduced diameter and proximal region 214' curves proximally inwardly to a reduced diameter to provide the foregoing advantages of bit 154. An abrasive coating such as a diamond coating can be provided on the bit 154 (and 154') to facilitate removal of particles from the vessel.

A coating can be provided over the rotatable shaft 153 and auger 186 in the same manner as described above.

In some embodiments, a solder can be used to attach the bit to the shaft, and the solder can form a smooth collar behind the bit to reduce vessel trauma during the back stroke (proximal movement) of the device. For example, the bit could be bullet shaped and have a solder at the proximal end to fill it out to a football like shape. In alternate embodiments, two opposite facing bits could be provided, either touching (or slightly spaced) connected with solder, to provide a football like shape. The bit facing surfaces, i.e., the proximal face of the distal bit and the distal face of the proximal bit, could be curved or flat.

Turning now to FIGS. 20 and 21A-21C which illustrates the housing 158 forming a handle for gripping by the clinician, the housing 158 include the hubs 190, 192 (described above), infusion tubing 206 extending from infusion port 196 of infusion hub 192 and exiting through a rear opening in the housing 158, aspiration tubing 208 extending from aspiration port 198 of aspiration hub 190 and extending through a rear opening in the housing 158, motor 236 and gear assembly 231. An on-off switch 226, connected to a circuit board within the housing that controls the motor, turns on the system to actuate the motor to rotate the rotatable shaft 153 (and attached abrasive tip 154). A speed control switch 228 enables the clinician to switch between two motor speeds—a fast and slow speed. The fast speed is for use of the device 150 to remove particles; the slower speed is for axial movement of the device 150 over a guidewire for removal of the device. In one embodiment by way of example, the fast speed is 140,000 rpm and the slow speed is 12,000 rpm, although other fast and slow speeds are also contemplated. More specifically, in certain clinical uses, when it is desired to remove the device 150 from the patient's body, the device 150 is slid proximally as the user holds the guidewire in place so it remains where it is in the body. This prevents the user from losing access to the target location. However, oftentimes there is a lot of static friction between the guidewire and the device so it is sometimes difficult to remove the device without also changing the position of the guidewire. Activating switch 228 to reduce the speed overcomes this by breaking the friction with the guidewire to allow the device to smoothly slide over the guidewire at a safe speed. The switch 228 is connected to a circuit board that controls the motor and is positioned within the housing 158. A wire can be wrapped around the speed switch at one end and the motor on the other end to catch a charge and redirect it to a ground instead of it passing through the device and turning on the motor. The motor casing acts as the ground.

A gear assembly 231 can be provided to multiply the motor speed, and in this embodiment multiples the motor speed by 4, although other multipliers are also contemplated. The large gear 230, supported in gear housing 234, is connected to the motor shaft 240. e.g., pressed onto the motor shaft, which extends from motor 236, and the small gear 242 is connected to the large gear 230. This small gear has bearings on both sides that sit in the gearbox base and cover. The gearbox cover is attached to the gearbox by the gearbox cover screws. The hubs screw directly into the gearbox cover. The rotatable shaft 153 is connected to the small gear 242 via hypotube 238. Hypotube 238 (and attached rotatable shaft 153), as shown, is axially offset from the motor 236 and motor shaft 240. Thus, by way of example, the motor 236 can be provided to spin at 35,000 rpm in use and 3,000 rpm for rapid exchange (i.e., removal), multiplied by 4 by the gear assembly 231 to spin at 140,000 rpm and 12,000 rpm, respectively.

In some embodiments, a connector extends from the housing for electrical connection to a wall outlet to power the device to effect rotation of the rotatable shaft and tip. In other embodiments, the power source is a battery contained in the housing.

The controller in the housing controls the DC motor, allowing it to spin at two pre-set speeds in a single direction, e.g., 35.000 rpm and 3,000 rpm as discussed above. The user can select the speed by the slide switch 228 on housing 158. Once the speed is selected, the separate power switch 226 is activated to enable rotation of the motor shaft to rotate the shaft 153 of the atherectomy device 150. The motor will quickly accelerate up to its pre-set speed. During use of the atherectomy device 150, the motor and control board are in constant communication so that as the device 150 experiences torque, the control board sends more current to keep the speed constant. This occurs until the torque limit is reached.

The control board limits motor torque by limiting the current supply to the motor at a specific threshold. When the threshold is reached, the motor continues to spin but pulls no more current than the threshold allows (meaning the speed will drop while the current stays constant—it does not immediately shut the motor down). If this torque causes the motor's rotational speed to decrease more than 5.000 rpm for greater than two seconds, the controller will terminate power to the motor, eliminating output torque from the motor. The motor will continue to rotate freely until a frictional torque overcomes the angular momentum of the motor. Note the motor spins in direction that the rotatable coil (shaft) opens up rather than the direction where the coil closes to avoid tightening of the coil and entanglement which could occur if the motor spinning caused winding of the shaft and coil. That is, if the coil has a right hand wind, since spinning counterclockwise opens the coil and spinning clockwise closes the coil, the coil would spin counterclockwise (in the direction of winding). With a left hand winding, the coil would spin clockwise.

Figure 4:
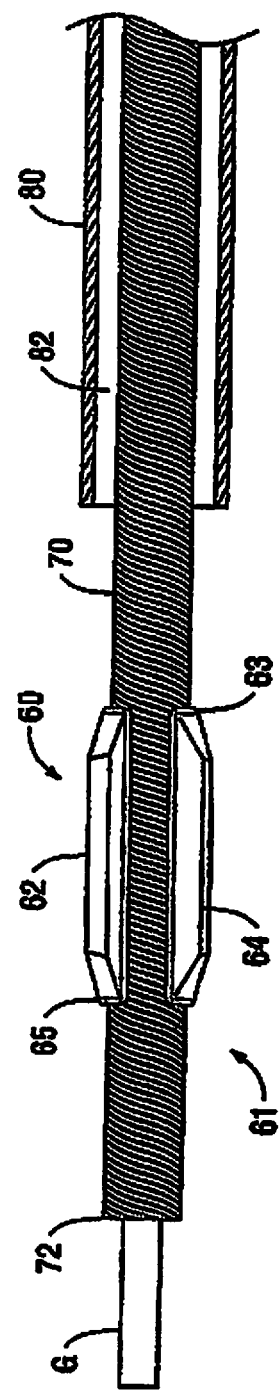
FIG. 4 is a partial cross-sectional view of the distal portion of an alternate embodiment of the atherectomy device of the present invention.
Figure 5:
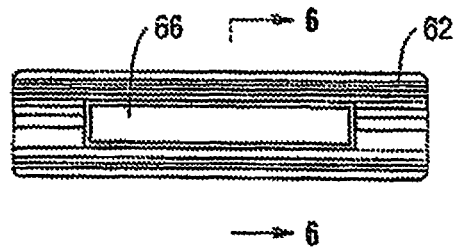
FIG. 5 is a cut away side view of the atherectomy bit of FIG. 4.
Figure 6:
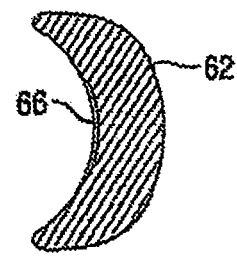
FIG. 6 is a transverse cross-sectional view taken along line 6-6 of FIG. 5.
Figure 7:
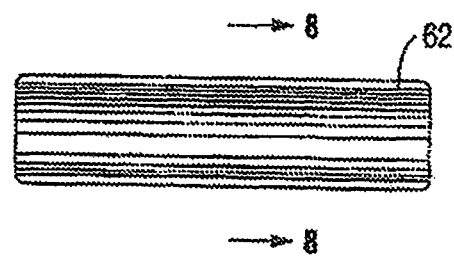
FIG. 7 is a cut away side view of the atherectomy bit of FIG. 4 showing the opposite side of the side shown in FIG. 5.
Figure 8:
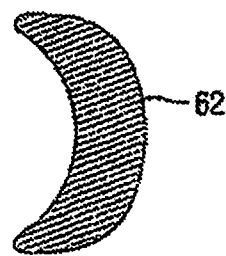
FIG. 8 is a transverse cross-sectional view taken along line 8-8 of FIG. 7.
Figure 16A:
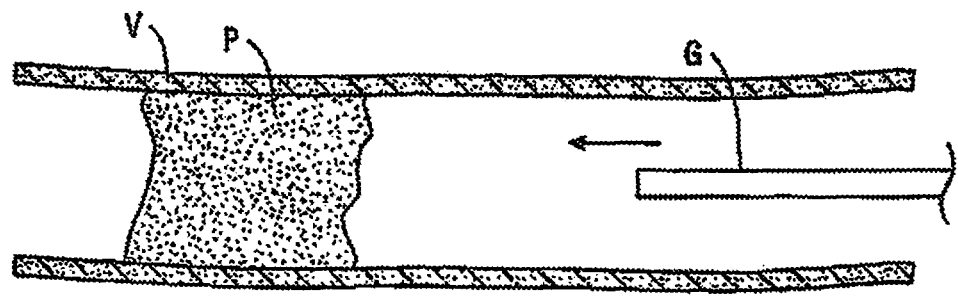
Figure 16B:
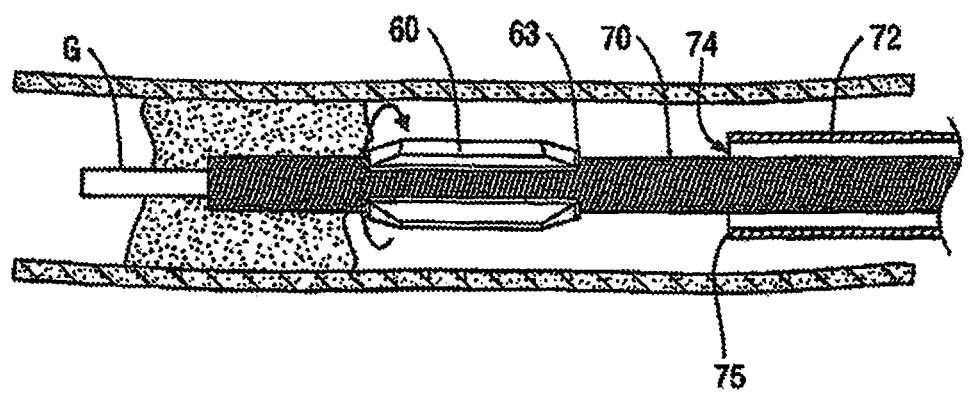
Figure 16C:
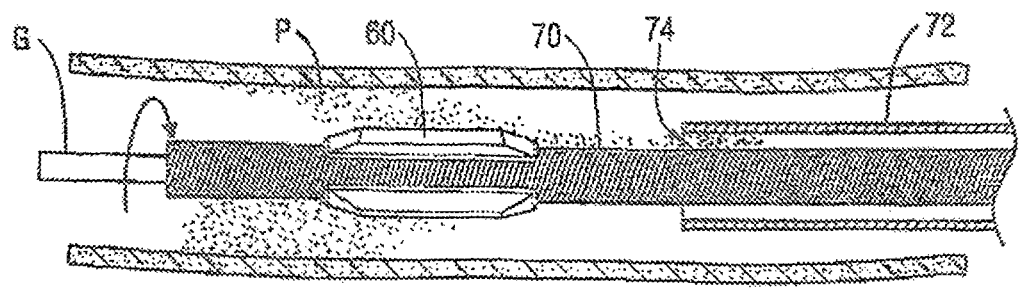
Figure 16D:
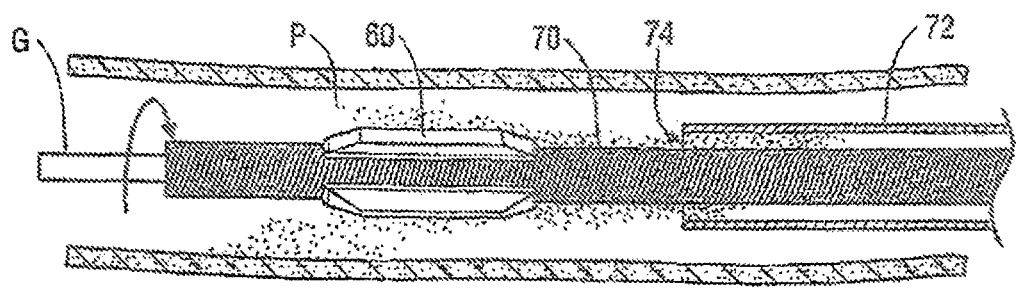
Figure 17:
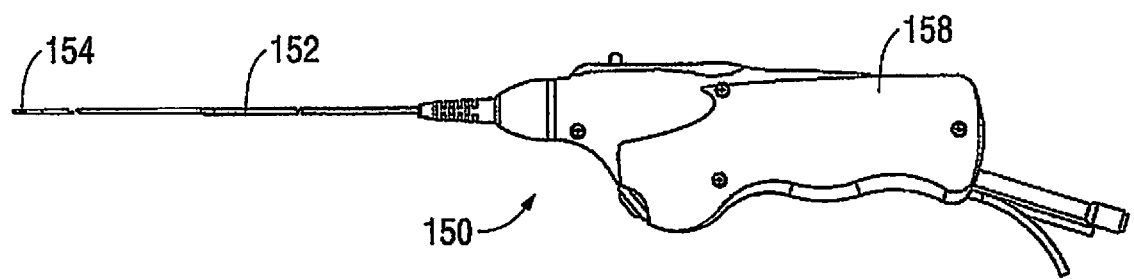
FIG. 17 is a side view of an alternate embodiment of the atherectomy device of the present invention.
Figure 25:
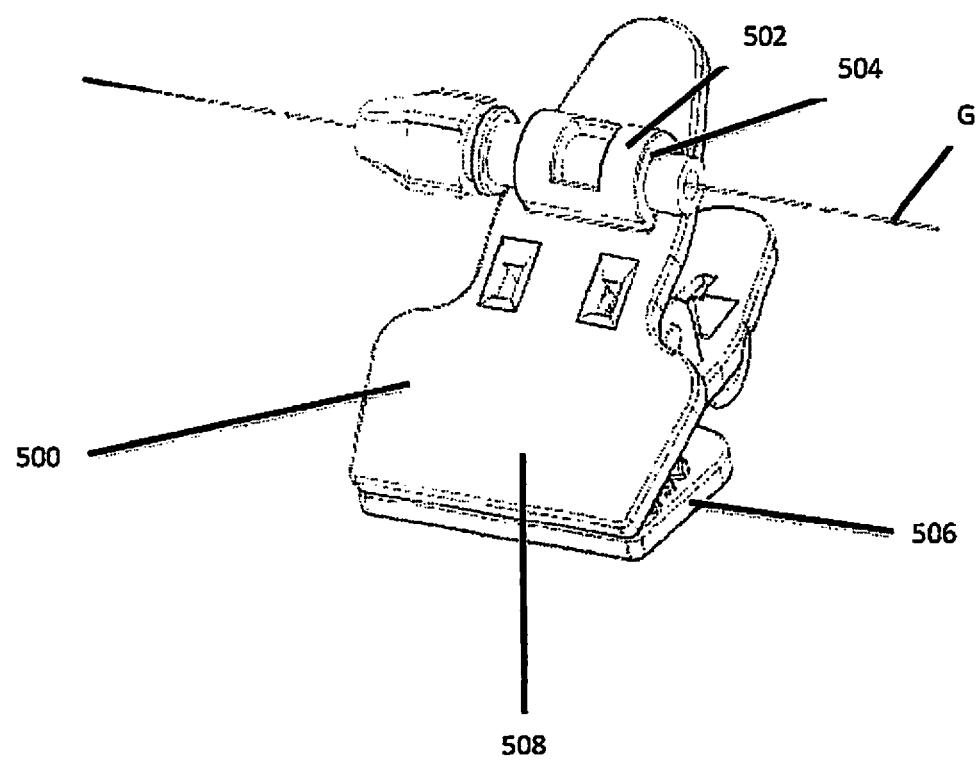
FIG. 25 is a perspective view of a torque clip of the present invention.

Use of the atherectomy tip of the present invention is illustrated in FIGS. 16A-16D. The tip 60 of FIG. 4 is shown in these drawings, it being understood that the other atherectomy devices and tips disclosed herein would be used in the same insertion and rotational manner. As shown in FIG. 16A, plaque "P" buildup on the interior wall of the vessel "V" has occluded the passageway through the vessel. Rotational shaft 70 with attached tip 60 (or any of the other tips disclosed herein) is inserted over guidewire G and by motorized rotation of flexible rotatable shaft 70 is rotated at high speed in the direction of the arrow in FIG. 16B to remove plaque which comes into contact with its outer surface. Aspiration is provided to aspirate the broken off particles through opening 74 in catheter 72. The fixed gap between the distal edge 75 of catheter 72 and the proximalmost edge 63 of tip 62 provides space for the particles to be suctioned through opening 74 and remains constant since the catheter 72 and shaft 70 do not move axially. Thus, the cut plaque and debris can be removed from the patient's body as the particles are dislodged by the rotating tip 60 as shown in FIG. 16C. As the plaque is removed, the device is continually advanced to continue to remove and aspirate the plaque as shown in FIG. 16D. As noted above, an auger like auger 44 or 96 can be provided in lieu of or in addition to an aspiration source FIG. 25 illustrates a torque clip 500 which mounts a torquer 502 for the guidewire. Guidewire G is inserted into the torquer 502 which is rotated to clamp (retain the guidewire). The torque clip 500 has an opening 504 dimensioned to receive the torquer 502 as shown. Preferably the guidewire G is inserted into the torquer 502 first, followed by insertion of the torquer 502 into torque clip 500. The hinged clip arms 506, 508 of torque clip 500 clip onto the drape or gown or other structure/material to retain the torque clip 500 and torquer 502 (and guidewire G).

Note the term axially fixed as used herein means the component does not move axially. However, axially fixed can also be considered to include substantially axially fixed such that significant axial movement is prevented so that the distance between the catheter and tip does not significantly change to affect aspiration. Similarly, a fixed gap can mean a substantially fixed gap so that the distance between the catheter and tip does not significantly change.

It should be appreciated that any of the tips described herein can be utilized with any of the rotatable shafts/catheters (outer members) disclosed herein.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An atherectomy device for removing deposits such as plaque from an interior of a vessel comprising:
   a housing;
   an outer member extending from the housing and having a distal end and a first lumen for fluid infusion to cool the device;
   an inner member having a distal end and positioned within the outer member, the inner member having a second lumen having an aspiration opening for aspiration of particles proximally within the second lumen, the first lumen in the outer member communicating with the second lumen for fluid infusion from the first lumen into the second lumen;
   a rotatable shaft positioned for rotational movement within the second lumen of the inner member; and
   a rotatable tip positioned at the distal region of the rotatable shaft and spaced distally from the distal end of the inner member, the rotatable tip rotatable by a motor to remove the deposits from the vessel for aspiration through the second lumen of the inner member;
   wherein, upon fluid infusion, fluid is blocked at a region spaced from the aspiration opening in the inner member and fluid is directed rearwardly during rotation of the rotatable shaft to provide a closed fluid system so fluid does not exit the first or second lumen into the body.

2. The atherectomy device of claim 1, wherein the rotatable tip is axially fixed with respect to the inner member to remain exposed during insertion and use of the atherectomy device.

3. The atherectomy device of claim 1, wherein the rotatable tip has a lumen to receive the rotatable shaft, the lumen having a first region having a first internal diameter and a second region having a second internal diameter greater than the first internal diameter, the second region being proximal of the first region.

4. The atherectomy device of claim 3, wherein the rotatable shaft includes a guidewire lumen for receiving a guidewire to enable over the wire insertion of the device, the guidewire lumen axially aligned with the lumen in the rotatable tip.

5. The atherectomy device of claim 1, further comprising an auger positioned on the rotatable shaft, the auger positioned proximally of the rotatable tip and extending along the rotatable shaft, wherein rotation of the rotatable shaft rotates the auger to move deposits macerated by the rotatable tip proximally into the inner member.

6. The atherectomy device of claim 5, wherein the augur aspirates the fluid received from the first lumen through the second lumen of the inner member.

7. The atherectomy device of claim 6, wherein a portion of the auger is exposed between a proximalmost edge of the rotatable tip and a distalmost edge of the inner member.

8. The atherectomy device of claim 6, wherein the auger is not exposed between the proximalmost end of the rotatable tip and a distalmost edge of the inner member.

9. The atherectomy device of claim 1, wherein the inner member comprises a first inner member and a second inner member positioned distal of the first inner member, and a gap is formed between the first and second inner members for entry of the fluid from the first lumen into the first inner member.

10. The atherectomy device of claim 9, wherein the first and second inner members are axially aligned.

11. The atherectomy device of claim 1, wherein fluid infusion is blocked by an end wall of the outer member terminating the first lumen proximal of the distal end of the outer member.

12. The atherectomy device of claim 1, wherein infusion of fluid from the first lumen is prevented from entering the vessel when aspiration is on and an auger on the rotatable shaft is rotated.

13. The atherectomy device of claim 1, wherein the inner member extends distally beyond a distalmost end of the outer member.

14. The atherectomy device of claim 1, wherein the outer member is coaxial with the inner member.

15. The atherectomy device of claim 1, wherein the outer member is formed of a proximal and distal catheter attached together.

16. The atherectomy device of claim 15, wherein a proximal end of the distal catheter terminates the first lumen to block the fluid infusion.

17. The atherectomy device of claim 1, wherein an opening in the inner member is radially aligned with an opening in the outer member.

18. The atherectomy device of claim 1, wherein the outer member includes a side opening located at a terminal wall.

* * * * *